(12) United States Patent
Hayes et al.

(10) Patent No.: US 10,543,137 B2
(45) Date of Patent: Jan. 28, 2020

(54) PATIENT SUPPORT APPARATUS WITH REMOTE COMMUNICATIONS

(71) Applicant: Stryker Corporation, Kalamazoo, MI (US)

(72) Inventors: Michael Joseph Hayes, Kalamazoo, MI (US); David Terrance Becker, Grand Rapids, MI (US); Annie Désaulniers, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 731 days.

(21) Appl. No.: 14/770,473

(22) PCT Filed: Mar. 12, 2014

(86) PCT No.: PCT/US2014/024672
§ 371 (c)(1),
(2) Date: Aug. 26, 2015

(87) PCT Pub. No.: WO2014/150970
PCT Pub. Date: Sep. 25, 2014

(65) Prior Publication Data
US 2016/0213537 A1   Jul. 28, 2016

Related U.S. Application Data

(60) Provisional application No. 61/906,961, filed on Nov. 21, 2013, provisional application No. 61/790,823, filed on Mar. 15, 2013.

(51) Int. Cl.
*A61G 7/018* (2006.01)
*G05B 15/02* (2006.01)
*G06F 19/00* (2018.01)

(52) U.S. Cl.
CPC ............. *A61G 7/018* (2013.01); *G05B 15/02* (2013.01)

(58) Field of Classification Search
CPC ........ G06Q 50/22; A61G 7/018; G05B 15/02; G06F 19/3406; G06F 19/3412; G06F 19/3418
See application file for complete search history.

(56) References Cited

U.S. PATENT DOCUMENTS 5,276,432 A    1/1994  Travis
5,603,034 A *  2/1997  Swanson ................. G06F 9/452
                                                    717/111
(Continued)

FOREIGN PATENT DOCUMENTS

WO       199427544    12/1994
WO       2012122002 A1  9/2012

OTHER PUBLICATIONS

PCT International Search Report regarding Application No. PCT/US2014/024672 filed Mar. 12, 2014, a counterpart of U.S. Appl. No. 14/211,613.

(Continued)

*Primary Examiner* — Kenneth M Lo
*Assistant Examiner* — Mohammad A Rahman
(74) *Attorney, Agent, or Firm* — Warner Norcross + Judd LLP

(57) ABSTRACT

A patient support apparatus includes a computer supported thereon that acts as a thin client for at least one network service available on a remote network to which the patient support apparatus has access. The thin client architecture of the patient support apparatus enables the patient support apparatus to dynamically change its functions, algorithms, features and other aspects more easily. The thin client architecture may be applied to generating alerts, performing maintenance functions, analyzing sensor data—including, (Continued)

but not limited to—weight sensors used to detect weight distributions on the patient support apparatus, implementing patient care protocols, performing patient assessments, accumulating information for billing, and monitoring patient movement. The patient support apparatuses may also function as local WiFi hotspots and/or as software access points to the healthcare network and/or the Internet. One or more Software-as-a-Service applications may run on the patient support apparatus.

22 Claims, 13 Drawing Sheets

(56) References Cited

U.S. PATENT DOCUMENTS

| | | | |
|---|---|---|---|
| 7,477,285 B1* | 1/2009 | Johnson | G06F 19/327 |
| | | | 348/143 |
| 7,699,784 B2 | 4/2010 | Wan Fong et al. | |
| 8,284,047 B2 | 10/2012 | Collins, Jr. et al. | |
| 8,413,271 B2 | 4/2013 | Blanchard et al. | |
| 8,618,918 B2 | 12/2013 | Tallent et al. | |
| 8,674,826 B2 | 3/2014 | Becker et al. | |
| 2003/0106930 A1* | 6/2003 | Williams | G06M 1/00 |
| | | | 235/103 |
| 2007/0027714 A1 | 2/2007 | Fenno | |
| 2007/0157385 A1* | 7/2007 | Lemire | A61G 7/005 |
| | | | 5/600 |
| 2007/0174964 A1 | 8/2007 | Lemire et al. | |
| 2008/0094207 A1* | 4/2008 | Collins, Jr. | A61B 5/1115 |
| | | | 340/539.12 |
| 2008/0126132 A1* | 5/2008 | Warner | A61B 5/0002 |
| | | | 705/3 |
| 2008/0221466 A1* | 9/2008 | Brauers | A61B 5/11 |
| | | | 600/508 |
| 2011/0030141 A1* | 2/2011 | Soderberg | A61G 7/0527 |
| | | | 5/600 |
| 2011/0144548 A1 | 6/2011 | Elliott et al. | |
| 2011/0247139 A1* | 10/2011 | Tallent | A61G 7/018 |
| | | | 5/613 |
| 2012/0026308 A1* | 2/2012 | Johnson | G06K 9/00369 |
| | | | 348/77 |
| 2012/0029951 A1* | 2/2012 | Baluta | G06Q 10/10 |
| | | | 705/4 |
| 2012/0124744 A1 | 5/2012 | Hornbach et al. | |
| 2012/0223821 A1 | 9/2012 | Collins, Jr. et al. | |
| 2012/0289787 A1* | 11/2012 | Kurgan | G06F 19/3418 |
| | | | 600/300 |
| 2012/0290319 A1* | 11/2012 | Saria | G06Q 50/24 |
| | | | 705/3 |
| 2013/0007078 A1* | 1/2013 | Wegener | G06F 7/483 |
| | | | 708/203 |
| 2013/0007740 A1* | 1/2013 | Kikuchi | H04L 41/5012 |
| | | | 718/1 |
| 2013/0205501 A1 | 8/2013 | Robertson et al. | |
| 2013/0253291 A1* | 9/2013 | Dixon | A47C 21/00 |
| | | | 600/323 |
| 2013/0283529 A1* | 10/2013 | Hayes | A61G 7/018 |
| | | | 5/600 |
| 2014/0039351 A1* | 2/2014 | Mix | A61B 5/1114 |
| | | | 600/587 |
| 2015/0025903 A1* | 1/2015 | Mueller-Wolf | G16H 10/20 |
| | | | 705/2 |
| 2015/0294380 A1* | 10/2015 | Kikuchi | G06Q 30/04 |
| | | | 705/34 |

OTHER PUBLICATIONS

PCT International Written Opinion regarding Application No. PCT/US2014/024672 filed Mar. 12, 2014, a counterpart of U.S. Appl. No. 14/211,613.

Anonymous, "Software as a Service", Wikipedia, the free encyclopedia, Mar. 7, 2013.

Beal, Vangie, "The Differences Beetween Thick & Thin Client Hardware", Webopedia, Jul. 6, 2006.

European Search Report dated Apr. 11, 2018, for European patent application EP14770611, corresponding to U.S. Appl. No. 14/770,473.

* cited by examiner

PATIENT SUPPORT APPARATUS WITH REMOTE COMMUNICATIONS

CROSS-REFERENCE TO RELATED APPLICATIONS

This application claims priority to U.S. provisional patent application Ser. No. 61/790,823 filed Mar. 15, 2013 by applicants Michael Hayes et al. and entitled PATIENT SUPPORT APPARATUS WITH REMOTE COMMUNICATIONS, as well as U.S. provisional patent application Ser. No. 61/906,961 filed Nov. 21, 2013 by applicants Michael Hayes et al. and entitled PATIENT SUPPORT APPARATUS WITH REMOTE COMMUNICATIONS, the complete disclosures of both of which are hereby incorporated herein by reference.

BACKGROUND OF THE INVENTION

The present invention relates to patient support apparatuses—such as beds, stretchers, cots, and the like—and more particularly to the electronics and communication systems on board the patient support apparatus.

SUMMARY OF THE INVENTION

The present invention provides systems and methods for improving the functionality, performance, adaptability, servicing, and/or usefulness of patient support apparatuses. In some embodiments, the patient support apparatus includes a computer that acts as a thin client for at least one network service, thereby enabling upgrades, modifications, improvements, and customizations of the one or more functions performed by the patient support apparatus. The network service may provide information, algorithms, data processing, and/or other features for the patient support apparatus that relate to such features as: monitoring patient movement (including turns), providing patient care assessments, implementing a patient care protocol, monitoring maintenance needs, analyzing sensor data, and implementing an exit alert system. In other embodiments, the patient support apparatus includes a platform for supporting at least one Software-as-a-Service (SaaS) application. In still other embodiments, the patient support apparatus is configured to act as a wireless hotspot for providing Internet access to one or more mobile devices, including, but not limited to, other patient support apparatuses, smart phones, computer tablets, and medical devices.

According to one embodiment, a patient support is provided that includes a frame, a support surface, a display, a transceiver, and a computer. The transceiver is adapted to communicate with a remote network. The computer is in communication with the display and the transceiver and is configured to act as a thin client with respect to at least one network service available on the remote network.

According to another embodiment, a patient support apparatus is provided that includes a frame, a support surface, a transceiver, a display, and a computer. The transceiver is adapted to communicate with a remote network. The computer is supported on the patient support apparatus and in communication with transceiver and the display. The computer is further adapted to control at least one function of the patient support apparatus and the computer includes a software platform for supporting at least one software-as-a-service (SaaS) application. The SaaS application is provided by a network service available on the remote network.

In other embodiments, the computer is adapted to run a plurality of thin client applications, wherein a first one of the thin client applications interacts with a first network service available on the remote network, and a second one of the thin client applications interacts with a second network service available on the remote network. Alternatively, the computer may be configured to support a plurality of SaaS applications, at first one of the SaaS applications being provided by a first network service available on the remote network and a second one of the SaaS applications being provided by a second network service on the remote network.

The network service or SaaS application may provide data for performing at least one of the following: assessing a bed sore risk of a patient; assessing a fall risk of a patient; determining when a patient may be about to exit the patient support apparatus; and determining if a patient has turned or not based on sensors positioned on board the patient support apparatus.

In other embodiments, the patient support apparatus includes a plurality of sensors adapted to detect when a patient may be about to exit the patient support apparatus, and the remote network service provides data to the computer for use in processing the outputs from the plurality of sensors. The patient support apparatus alternatively may include a plurality of sensors adapted to provide information indicative of whether a patient has turned or not while positioned on the support surface, and the network service provides data to the computer for use in processing outputs from the plurality of sensors. In some embodiments, the sensors are load cells adapted to detect the weight distribution of the patient on the support surface.

The computer may forward sensor data to the network service for processing and receive processed data back from the network service, wherein the processed data is a result of the processing of the signals received from the computer. The forwarded sensor data may include information generated from a plurality of force sensors. Such information may enable the network service to determine whether or not the patient has turned while positioned on the patient support apparatus, whether a patient may be about to exit from the support surface, and/or whether a patient on the support surface is asleep or awake.

The network service and/or SaaS application may generate billing information based on usage of the patient support apparatus. The network service and/or SaaS application may alternatively provide information relating to how often a patient supported on the patient support apparatus should be turned, and/or other information relating to a patient care protocol.

The network service may communicate with at least one other network service on the remote network. The other network service may be any one or more of the following: an electronic medical records service; a caregiver workflow service; an admission, discharge and tracking (ADT) service; a real time location service; and/or a caregiver communication service.

The network service and/or SaaS application may monitor infection data.

The network service and/or SaaS application may also control at least a portion of the screen space of the display mounted on the patient support apparatus. The network service and/or SaaS may also control other aspects of the patient support apparatus, such as, but not limited to, alerts, movement, settings, and/or communications.

The network service may be adapted to forward one or more algorithms to the patient support apparatus computer that are used to process one or more outputs from sensors positioned on board the patient support apparatus.

In some embodiments, the transceiver is a WiFi transceiver and the remote network is an Ethernet. In other embodiments, the remote network is the Internet.

The patient support apparatus is any of a bed, a stretcher, a cot, a recliner, and/or an operating table. The patient support apparatus may further include an elevation adjustment mechanism adapted to raise and lower the frame, at least one motor adapted to pivot a section of the support surface about a generally horizontal axis, a plurality of side rails coupled to the frame, and a control panel having controls for controlling the elevation adjustment mechanism and the motor. Still further, the patient support apparatus may include a headboard, a footboard, a plurality of wheels, and a brake for selectively locking and unlocking the wheels. The display on the patient support apparatus is, in some embodiments, a touch screen.

In other embodiments, the network service is configurable by one or more employees of the healthcare facility in which the patient support apparatus is positioned such that the employees are able to configure what information is provided to the patient support apparatus by the network service. The network service may provide a list of questions for assessing an aspect of a patient supported on the patient support apparatus. The list of questions may be controllable by one or more employees of the healthcare facility. The patient support apparatus computer receives the list of questions from the network service and displays the list of questions on the display. The list of questions may provide an assessment of a patient's susceptibility to developing bed sores, or an assessment of a patient's fall risk.

A movement counting device may also be positioned on the patient support apparatus. The movement counting device counts the number of times a component on the patient support apparatus moves, and the computer issues a maintenance alert if the number of times the component on the patient support apparatus moves exceeds a threshold. The threshold may be provided by the network service.

An exit detection system is included on the patient support apparatus in some embodiments. The exit detection system includes a controller and a plurality of load cells positioned on the support surface that are adapted to detect weight support on the support surface. The controller calculates a center of gravity of weight positioned on the support surface, and the computer forwards the calculated centers of gravity to the network application. In some embodiments, the computer forwards to the network service the centers of gravity calculated both moments before, and moments after, a patient exits the patient support.

In other embodiments, the SaaS application determines whether a patient has turned or not while positioned on the support surface, based on the outputs from a plurality of sensors on the patient support apparatus. Alternatively, or additionally, the SaaS application may determine whether a patient is about to exit from the support surface, or whether a patient on the support surface is asleep or awake. Still further, the SaaS application may indicate how often a patient supported on the patient support apparatus should be turned, or it may monitor infection data, or it may provide a list of questions for assessing an aspect of a patient supported on the patient support apparatus. When providing such a list, the questions may be controllable by the employees of the healthcare facility, and the list is displayable on the patient support apparatus display. The list of questions may relate to a patient's susceptibility to developing bed sores, or a patient's fall risk, or to other aspects of a patient.

The SaaS, in some embodiments, controls at least one circumstance under which the computer should issue an alert.

According to another embodiment, a patient support apparatus is provided that includes a frame, a support surface, first and second actuators, and a controller. The first and second actuators are adapted to move first and second components on the patient support apparatus, respectively. The controller controls the first and second actuators and counts the number of times the first actuator is actuated and the number of times the second actuator is actuated. The controller further compares the first count to a first threshold and the second count to a second threshold. If either the first count exceeds the first threshold, or the second count exceeds the second threshold, the controller issues a maintenance alert.

The maintenance alert may be forwarded via a transceiver to a network service available on a remote network. The remote network may be a local area network within the healthcare facility, or multiple buildings of the healthcare facility, or it may be a wide area network, or it may be the Internet. The first actuator may be one of a lift actuator adapted to raise and lower the frame, a tilt actuator for changing a tilt of a pivotable section of the support surface, or a brake actuator for turning on and off a brake on the patient support apparatus. The first and/or second thresholds may be received by the controller from the remote network.

A third actuator may be included on the patient support apparatus that is adapted to move a third component on the patient support apparatus, wherein the controller totals a number of times the third actuator is actuated and issues the maintenance alert if the third number exceeds the third threshold. The controller may be a computer that includes a software platform for supporting at least one software-as-a-service (SaaS) application, wherein the SaaS application compares the first, second, and third numbers to the first, second, and third thresholds, respectively.

The controller may forward the first and second numbers to the network service. The network service may be adapted to gather the first and second numbers from a population of patient support apparatuses, analyze the first and second numbers, and use the analysis for determining the first and second thresholds.

The maintenance alert may be displayed on the display mounted on the patient support apparatus.

According to another embodiment, a patient support apparatus is provided that includes a frame, a support surface, a display, a transceiver, and a computer. The transceiver is adapted to communicate with a remote network. The computer is in communication with the transceiver and configured to act as a wireless software access point for the remote network for devices positioned within communication range of the computer.

The transceiver may follow the standards of IEEE 802.11, or it may communicate using other communication standards. The patient support apparatus may also include a second transceiver different from the first transceiver wherein the second transceiver is adapted to communicate with the computer and at least one device so that the at least one device can use the computer as a software access point. The second transceiver may be a Bluetooth transceiver.

The devices which may communicate the wireless software access point include other patient support apparatuses, smart phones, computer tablets, and/or personal computing devices. The computer configured to act as a wireless software access point may be adapted to provide Internet access to one or more of the devices.

According to another embodiment, a patient support apparatus is provided that includes a frame, a support surface supported on the frame, a transceiver, a sensor, and a controller. The transceiver is adapted to communicate with a remote network, and the controller is in communication with the sensor and transceiver. The controller is adapted to transmit to the remote network, via the transceiver, a request for a software application when the controller determines that a situational condition of the patient support apparatus exists. The controller determines the existence of the situational condition by using the output of the sensor.

According to other embodiments, the situational condition may be any one or more of the following: a device is positioned in detectable proximity to the patient support apparatus; a person is positioned in detectable proximity to the patient support apparatus; and/or the patient support apparatus is positioned within a detectable location within a healthcare facility. In some embodiments, the sensor is adapted to detect the detectable proximity of either or both of the device or the person, or the detectable location of the patient support apparatus.

In one embodiment, the situational condition is the presence of a mattress on the patient support apparatus. In such embodiments, the controller may be configured to identify a type of the mattress based on information received from the sensor. The controller may also be configured to forward the type of mattress in the request for a software application to the remote network. The request for a software application may be a request for mattress software designed to be used by the controller to communicate with the mattress. The mattress software is designed to be used by the controller to control at least one aspect of the mattress. The controller may be configured to receive the mattress software from the remote network and to run the mattress software after being received from the remote network. The mattress software may be a thin client application, a thick client application, or a purely local application.

In another embodiment, the sensor is an RF ID sensor adapted to detect the presence of an RF ID tag positioned within a proximity to the RF ID sensor.

The request for a software application may be a request for patient support apparatus software designed to be used by the controller to control at least one aspect of the patient support apparatus. In some embodiments, the patient support apparatus software controls movement of at least one component of the patient support apparatus.

The situational condition may be the presence of a patient entertainment device within a vicinity of the patient support apparatus. The patient entertainment device could be a television where the request for a software application is a request for television control software designed to control the television. The controller may use the television control software in conjunction with at least one control positioned on the patient support apparatus, wherein the control is adapted to allow a patient positioned on the patient support apparatus to control an aspect of the television.

The situational condition may also be the presence of a patient biological sensor within a vicinity of the patient support apparatus. The software application may include interface software adapted to be executed by the controller to allow the controller to communicate directly with the patient biological sensor.

The situational condition may also be the presence of a person positioned in detectable proximity to the patient support apparatus. In such cases, the request for a software application may be for patient support apparatus software designed to be executed by the controller to control at least one aspect of a user interface positioned on the patient support apparatus and operable by the person. The user interface may include at least one touch screen display positioned on the patient support apparatus. The patient support apparatus software controls at least one icon displayed on the touch screen display, in some embodiments. In some embodiments, the patient support apparatus software performs at least one diagnostic test of a component of the patient support apparatus.

The situational condition may also be the presence of a second patient support apparatus within the vicinity of the patient support apparatus. In such cases, the request for a software application is a request for communication software designed to allow the controller to communicate with the second patient support apparatus.

In still another embodiment, a patient support apparatus is provided that includes a frame, a support surface, a transceiver, and a controller. The transceiver communicates with a remote network, and the controller is in communication with the transceiver. The controller is able to receive from a network service hosted on the remote network a software application in response to an association being established between the patient support apparatus and at least one of a device, a person, or a location.

According to other embodiments, the network service is in communication with a real-time locating system installed in a healthcare facility in which the patient support apparatus is located. The association may be established by the network service based upon information received from the real-time locating system, or based upon information received from the patient support apparatus. Still further, the network service may establish the association based upon the patient support apparatus being within a threshold proximity to the at least one of a device, a person, or a location.

In some embodiments, the association is established between the patient support apparatus and a mattress positioned on the patient support apparatus, wherein the software application being is to be executed by the controller to enable the controller to control at least one aspect of the mattress.

In other embodiments, the association is established between the patient support apparatus and a patient entertainment device positioned within a common room with the patient support apparatus, wherein the software application is adapted to be executed by the controller to enable a control positioned on the patient support apparatus to control an aspect of the entertainment device. The entertainment device may be a television.

In other embodiments, the association is established between the patient support apparatus and a patient biological sensor, wherein the software application is adapted to be used by the controller when communicating with the patient biological sensor.

In still other embodiments, the association is established between the patient support apparatus and a second patient support apparatus, wherein the software application is adapted to allow the controller to communicate with the second patient support apparatus.

In still other embodiments, the association is established between the patient support apparatus and a person, wherein the software application is adapted to be used by the controller to control at least one aspect of a user interface positioned on the patient support apparatus and operable by the person.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and is capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION OF THE EMBODIMENTS

Figure 1:
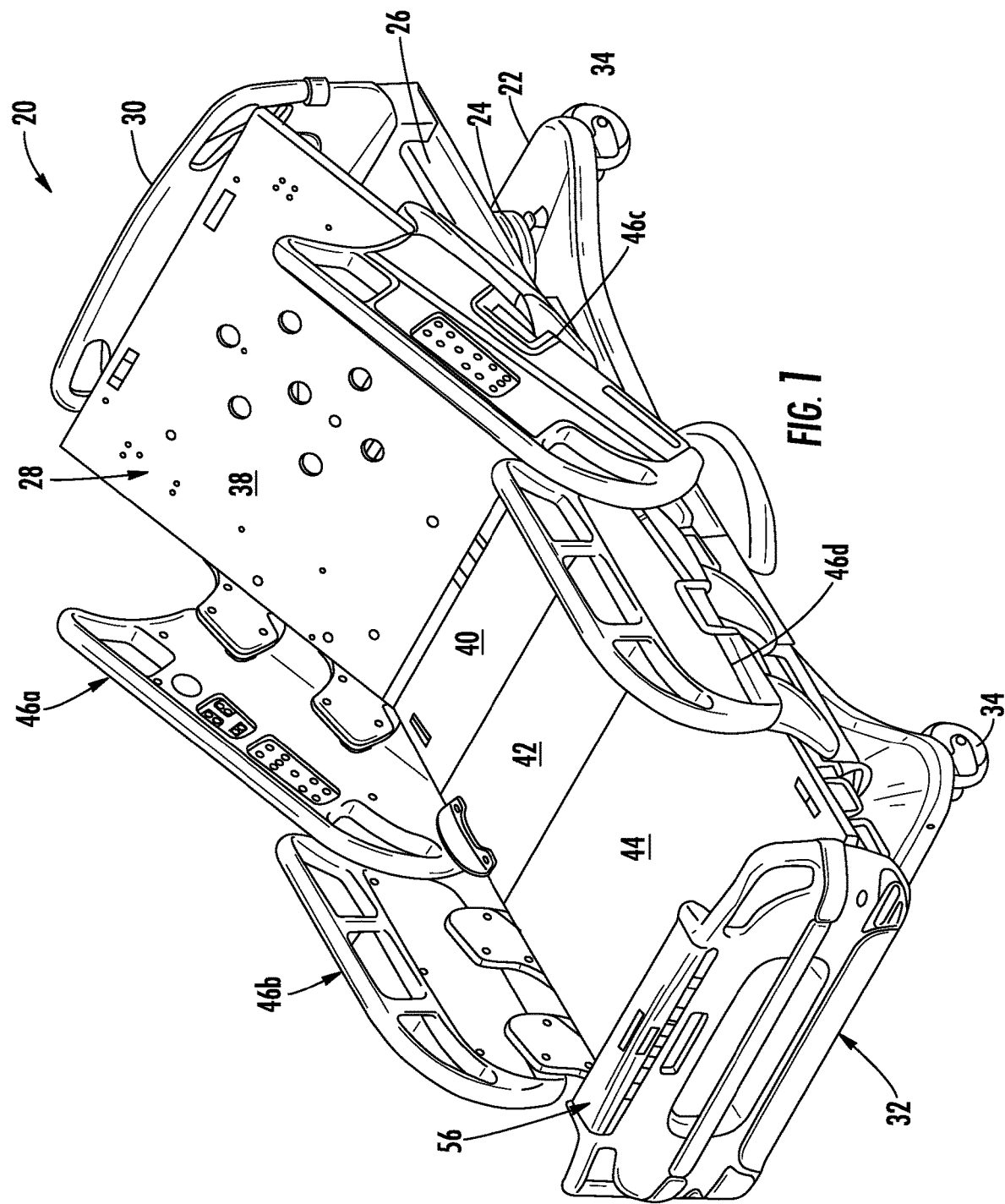
FIG. 1 is a perspective view of an illustrative patient support apparatus that is able to implement any one or more of the various features of the present invention.

The inventive features, functions, and systems described herein are applicable to patient support apparatuses, such as beds, cots, stretchers, operating tables, recliners, and the like. FIG. 1 shows an illustrative patient support apparatus 20—in this case a hospital bed—that may incorporate any one or more of the features, functions, and/or system described herein.

More particularly, FIG. 1 illustrates a patient support apparatus 20 that includes a base 22, a pair of elevation adjustment mechanisms 24, a frame or litter assembly 26, a patient support surface or deck 28, a headboard 30, and a footboard 32. Base 22 includes a plurality of wheels 34 that can be selectively locked and unlocked so that, when unlocked, patient support apparatus 20 is able to be wheeled to different locations. Elevation adjustment mechanisms 24 are adapted to raise and lower frame 26 with respect to base 22. Elevation adjustment mechanisms 24 may be hydraulic actuators, electric actuators, or any other suitable device for raising and lowering frame 26 with respect to base 22. In some embodiments, elevation adjustment mechanisms 24 operate independently so that the orientation of frame 26 with respect to base 22 may also be adjusted.

Frame 26 provides a structure for supporting patient support surface 28, headboard 30, and footboard 32. Patient support surface 28 provides a surface on which a mattress, or other soft cushion, is positionable so that a patient may lie and/or sit thereon. Patient support surface 28 is made of a plurality of sections, some of which are pivotable about generally horizontal pivot axes. In the embodiment shown in FIG. 1, patient support surface 28 includes a head section 38, a seat section 40, a thigh section 42, and a foot section 44. Head section 38, which is also sometimes referred to as a Fowler section, is pivotable between a generally horizontal orientation (not shown in FIG. 1) and a plurality of raised positions (one of which is shown in FIG. 1). Thigh section 42 and foot section 44 may also be pivotable in some embodiments.

In addition to the aforementioned components, patient support apparatus 20 includes four side rails: a right head side rail 46a, a right foot side rail 46b, a left head side rail 46c and a left foot side rail 46d. Side rails 46 are be movable between a raised position and a lowered position. In the configuration shown in FIG. 1, all four of the side rails 46 are raised.

The physical construction of any of base 22, elevation adjustment mechanisms 24, frame 26, patient support surface 28, headboard 30, footboard 32, and/or side rails 46 may be the same as disclosed in commonly assigned, U.S. Pat. No. 7,690,059 issued to Lemire et al., and entitled HOSPITAL BED, the complete disclosure of which is incorporated herein by reference; or as disclosed in commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosure of which is also hereby incorporated herein by reference; or as embodied in the commercially available S3 bed sold by Stryker Corporation of Kalamazoo, Mich., and document in the Stryker Maintenance Manual for Stryker's MedSurg Bed, Model 3002 S3, (doc. 3006-109-002 Rev D), published in 2010, the complete disclosure of which is also hereby incorporated herein by reference. The construction of any of base 22, elevation adjustment mechanisms 24, frame 26, patient support surface 28, headboard 30, footboard 32 and/or side rails 46 may also take on forms different from what is disclosed in these documents.

Figure 2:
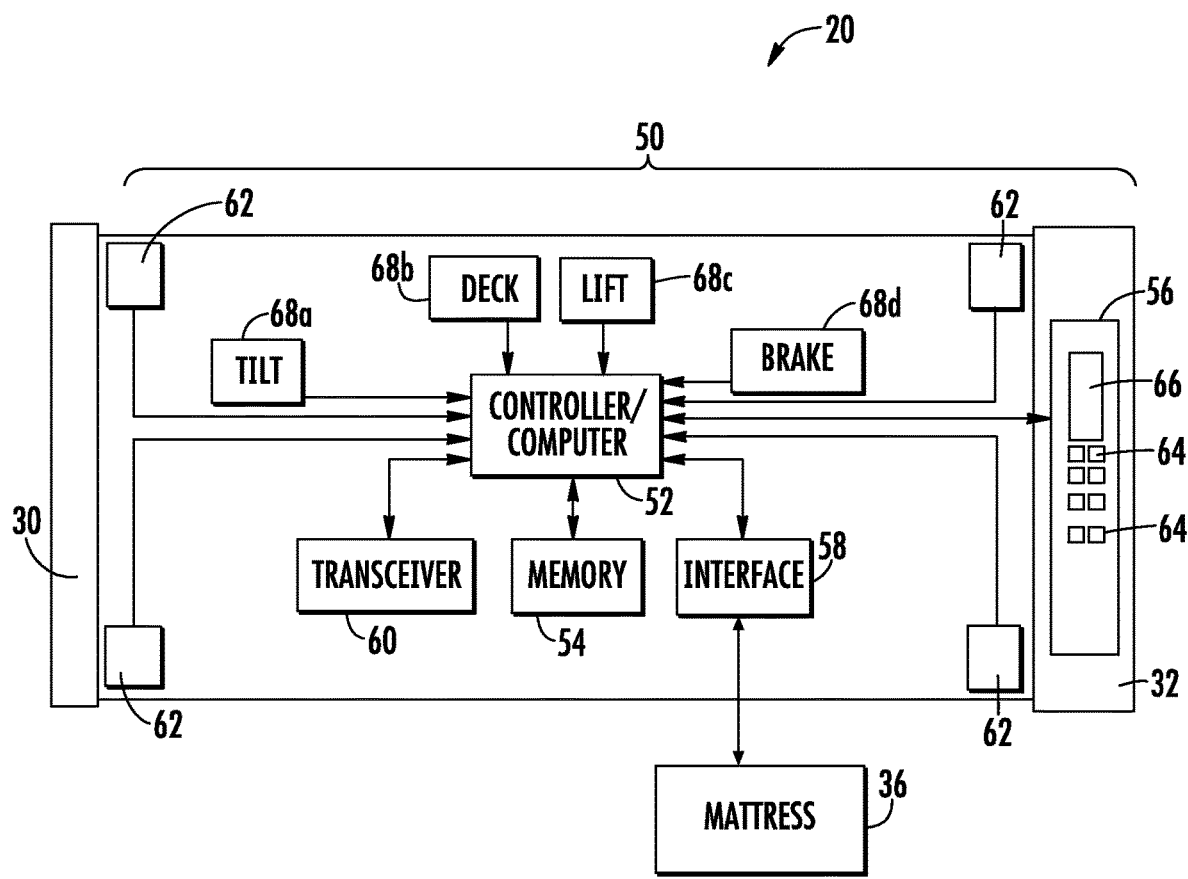
FIG. 2 is a plan view diagram of a control system according to one embodiment that may be implemented into various patient support apparatuses, such as, but not limited to, the one of FIG. 1.

FIG. 2 illustrates a plan view diagram of a control system 50 for patient support apparatus 20. Control system 50 includes a computer or controller 52, a memory 54 in communication with the controller 52, a user interface 56, at least one sensor or device interface 58, at least one transceiver 60, and four force sensors or load cells 62. In the embodiment shown in FIG. 2, control system 50 further includes a plurality of actuators 68, such as a tilt actuator 68a, a deck actuator 68b, a lift actuator 68c, and a brake actuator 68d. Other actuators may also be included.

The components of control system 50 communicate with each other using conventional electronic communication techniques. In one embodiment, controller 52 communicates with memory 54, user interface 56, and load cells 62 using I-squared-C communications. Other types of serial or parallel communication can alternatively be used. In some other embodiments, different methods may be used for different components. For example, in one embodiment, controller 52 communicates with user interface 56 via a Controller Area Network (CAN) or Local Interconnect Network (LIN), while it communicates with memory 54, actuators 68, and load cells 62 using I squared C. Still other variations are possible.

User interface 56 includes a plurality of buttons 64 that a caregiver presses in order to control various features of the patient support apparatus, such as, but not limited to, raising and lowering the height of frame 26 via lift actuators 68a and/or 68c, pivoting one or more of support surface sections 28 via one or more deck actuators 68b, turning on and off a brake (not shown) via brake actuator 68d, controlling a scale system integrated into the patient support apparatus, controlling an exit alert system integrated into the support apparatus 20, and/or controlling other features of the patient support apparatus 20. User interface 56 further includes a display 66 integrated therein. Display 66 is a touchscreen display capable of displaying text and/or graphics and sensing the location that a user's finger touches the display, although it will be understood that display 66 could be modified to be a normal LCD display without touchscreen capabilities that use hard or soft buttons to interact therewith, or still other types of displays.

Controller/computer 52 includes one or more microcontrollers, microprocessors, and/or other programmable electronics that are programmed to carry out the functions described herein. It will be understood that controller 52 may also include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions on patient support apparatus 20, or they may reside in a common location on patient support apparatus 20. When physically distributed, the components may communicate using any suitable serial or parallel communication protocol, such as, but not limited to, CAN, LIN, Firewire, I-squared-C, RS-232, RS-485, etc.

Force sensors 62 are, in some embodiments, any conventional load cells, or similar force measuring sensors, that are positioned to detect the amount of downward force exerted by patient support deck 28, and any objects, patient(s), and/or other persons that are exerting downward forces on support deck 28, whether due to gravity or due to other causes. In some embodiments, the force sensors 62 may be configured so that, in addition to downward forces, they are also able to detect forces exerted in generally horizontal directions (both laterally and longitudinally).

When implemented as load cells, the physical arrangement of force sensors 62 may take on a conventional arrangement, such as those found in a variety of different conventional hospital beds. For example, in one embodiment, the position and physical construction of load cells 62 are the same as that found in the S3® bed sold by Stryker Corporation of Kalamazoo, Mich. These physical details are described in detail in the Stryker Maintenance Manual for Stryker's MedSurg Bed, Model 3002 S3, (doc. 3006-109-002 Rev D), published in 2010, the complete disclosure of which has already been incorporated herein by reference.

Controller 52 is in communication with each of four load cells 62 and receives the outputs from load cells 62. Load cells 62 are positioned adjacent each corner of the patient support surface 28 and cumulatively sense the entire weight of a patient, other person, and/or objects positioned on the patient support surface 28. In one arrangement, the load cells are positioned such that one load cell 62 is positioned adjacent each corner of a load frame (not shown), and the load cells 62 detect forces exerted by a patient support frame upon the load frame (through the load cells). While the construction of the load frame and patient support frame may vary, one example is disclosed in the commonly assigned U.S. Pat. No. 7,690,059 mentioned above and incorporated herein by reference. Another example is disclosed in the Stryker Maintenance Manual for the Model 3002 S3 MedSurg Bed, which has also already been incorporated herein by reference. Other constructions of the frames and positions of the load cells may also be used.

Transceiver 60 is used by controller 52 for forwarding selected information from control system 50 to other devices, such as a healthcare facility computer network 72 (FIG. 3), or another recipient. Healthcare facility computer network 72 is often, though not necessarily always, an Ethernet, and it will be understood that computer network 72 can take on other forms. In one embodiment, transceiver 60 is a WiFi radio transmitter and receiver that is capable of communicating with a wireless access point 88 (FIG. 3) of the hospital network 72 in accordance with IEEE 802.11 standards, or in accordance with other standards. More specific uses of transceiver 60 are discussed below.

It will be understood by those skilled in the art that use of the term "transceiver" throughout this specification is not intended to be limited to devices in which a transmitter and receiver are necessarily within the same housing, or share some circuitry. Instead, the term "transceiver" is used broadly herein to refer to both structures in which circuitry is shared between the transmitter and receiver, and transmitter-receivers in which the transmitter and receiver do not share circuitry and/or a common housing. Thus, the term "transceiver" refers to any device having a transmitter component and a receiver component, regardless of whether the two components are a common entity, separate entities, or have some overlap in their structures.

Interface 58 is used to communicate with one or more electronic devices that are positioned on, or in the vicinity of, patient support apparatus 20. As shown in FIG. 2, interface 58 is configured to communicate with a mattress 36 that is positionable on top of patient support deck 28. Mattress 36 may be a mattress of the type disclosed in commonly assigned U.S. patent applications Ser. Nos. 61/696,819 and 61/697,010, entitled INFLATABLE MATTRESS AND CONTROL METHODS and PATIENT SUPPORT, respectively, both of which were filed on Sep. 5, 2012, the complete disclosures of both of which are hereby incorporated herein by reference. Such mattresses include a plurality of inflatable bladders whose inflation pressure is controllable by one or more controllers contained with the mattress. The mattress may further include a plurality of sensors used for detecting information about the status of the mattress, such as, but not limited to, one or more depth sensors, fluid pressure sensors, temperature sensors, patient interface pressures sensors, and/or humidity sensors.

In some embodiments, interface 58 is a Controller Area Network connection that communicates with mattress 36, while in other embodiments, interface 58 takes on other forms. In one embodiment, interface 58 is a wireless connection, such as that disclosed in commonly assigned U.S. patent application Ser. No. 13/296,656 filed Nov. 15, 2011 by applicants Guy Lemire et al. and entitled PATIENT SUPPORT WITH WIRELESS DATA AND/OR ENERGY TRANSFER, the complete disclosure of which is hereby incorporated herein by reference.

In some embodiments, interface 58 may be used to communicate with a flexible pressure sensing mat (not shown), either in addition to, or in lieu of, mattress 36. Such flexible pressure sensing mats are positioned on top of, underneath, or integrated into, mattress 36. Such pressure sensing mats are used to detect the interface pressures between the patient and the support surface the patient is positioned on, and can be useful for monitoring such pressures so as to avoid the development, or potential development, of bed sores. In one embodiment, a flexible pressure sensing mat of the type disclosed in commonly assigned PCT patent application serial number PCT/US12/27402, filed Mar. 2, 2012 by Stryker Corporation, and entitled SENSING SYSTEM FOR PATIENT SUPPORTS, the complete disclosure of which is hereby incorporated herein by reference. Such a flexible pressure sensing mat may forward pressure information, including but not limited to, a patient interface pressure distribution map, to controller 52, and/or any other information that is detectable by the flexible pressure sensing mat (such as, but not limited to, patient heart rate, patient respiration rate, patient position, patient orientation, patient movement—including patient turns, and other information).

In still other embodiments, control system 50 may include more than one interface 58, and each interface 58 may be of the same or different type (e.g. some may be wired, some may be wireless, or they both may be wired or wireless but use different communication protocols). In one embodiment, control system 50 includes a near field communications transceiver that communicates in any of the manners, and with any of the devices, disclosed in commonly assigned U.S. patent application Ser. No. 13/802,992, filed Mar. 14, 2013 by applicants Michael Hayes et al, and entitled COMMUNICATION SYSTEMS FOR PATIENT SUPPORT APPARATUSES, the complete disclosure of which is hereby incorporated herein by reference. Such a near field communications transceiver can be used for establishing associations between patient support apparatus 20 and other objects (e.g. medical devices, mattress 36, patients or caregivers wearing near field ID tags, or other items).

Such associations are forwarded to controller 52. In addition to near field communications, interface 58 may also carry out far field communications using one or more transceivers that are separate from transceiver 60. Such separate transceivers typically communicate using a separate communications protocol than that of transceiver 60. For example, in one embodiment, transceiver 60 using WiFi communications, while the one or more transceivers of interface 68 use Bluetooth and/or ZigBee communications, or other protocols.

Interface 58 may also be configured to communicate with other devices, such as any of the devices disclosed in commonly assigned U.S. patent application Ser. No. 13/570,934 filed Aug. 9, 2012, by applicants Michael Hayes et al. and entitled PATIENT SUPPORT APPARATUS WITH IN-ROOM DEVICE COMMUNICATION, the complete disclosure of which is hereby incorporated herein by reference. When so configured, interface 58 forwards data from the devices it is in communication with to controller 52. Such devices include, but are not limited to, hand washing stations, medical devices, and patient and/or caregiver ID tags. The forwarded information includes associations with, and/or identifications of, medical devices, caregiver and/or patient identifications, and information about the use or lack of use of handwashing stations.

Controller 52 is configured to create a software environment in which one or more thin client applications are able to operate. Such thin client applications communicate with one or more network services 76, 76a, 76b, etc. (FIG. 3), which are available on one or more remote networks, such as healthcare facility network 72 and/or the Internet 74. Controller 52 is therefore able to support one or more thin client applications 78 where a substantial portion of the computational workload carried out by the application is done remotely via one or more network services 76. The term "thin client" as used herein shall be given its ordinary and accustomed meaning in the field of computer science and software. In general, a thin client refers to a computer or computer program which depends substantially on another computer or, in this case, one or more network services 76, to fulfill its programmed computational functions.

Although controller 52 is configured to create a thin client software environment, controller 52 does not, in at least some embodiments, exclusively support thin client applications. That is, in some embodiments, controller 52 is configured to support both fat and thin client applications, as well as applications that are purely local. Controller 52, however, is configured such that at least one software application can be supported thereon as either a thin client or a fat client, while at least one other software application is supported thereon that is purely local.

In still other embodiments, separate controllers 52 may be implemented for the different software environments. That is, in one embodiment, a controller 52 may support thin client applications exclusively, while another controller supports fat client applications exclusively, while one or more additional controllers support purely local applications.

Examples of the various thin client, thick client, and local applications that may operate via controller 52 will be discussed in greater detail below, but such applications include any one or more of the following: patient assessment applications (e.g. assessing a patient's risk of falls, assessing a patient's risk of bed sores, etc.); sensor monitoring and/or data collection applications (e.g. gathering load cells outputs—such as patient position, center of gravity, weight, weight distribution, patient movement, etc.—gathering pressure mat outputs, gathering vital sign readings, gathering data from medical devices associated with support apparatus 20 and/or the patient assigned to the support apparatus 20); maintenance monitoring/scheduling applications (e.g. monitoring the actual usage of various components on support apparatus 20 for maintenance purposes); billing applications (e.g. patient usage of support apparatus 20 features, medical device usage, patient presence on support apparatus 20); and/or patient care protocol management applications (e.g. defining, implementing, and/or monitoring of patient care protocols, such as protocols for preventing patient falls, protocols for preventing bed sores, protocols for turning patients, protocols for preventing ventilator-associated-pneumonia (VAP), protocols for containing or reducing infections, etc.).

Including one or more thin or thick client applications operable on controller 52 offers a variety of advantages over traditional patient support apparatuses. Conventional patient support apparatuses typically include one or more computers or controllers that carry out various control functions or protocol features purely locally. While some conventional patient support apparatuses are capable of forwarded information to a server on a remote network, the software carrying this out is purely local. That is, such conventional patient support apparatuses do not include any applications whose features, functions, algorithms, or other computational aspects are carried out at least partially remotely. By having purely local software or applications, conventional patient support apparatuses have features that are generally standard from one healthcare facility to another, are difficult to upgrade, cannot be custom tailored to healthcare facilities, and/or do not easily allow new applications to be added. As will be explained in greater detail below, controller 52's support of thin and thick client applications enables healthcare institutions that purchase patient support apparatus 20 to more easily custom tailor the controls on the patient support apparatus 20, add new functions or features, automatically follow improved algorithms, and adapt more easily to changing user requirements.

Figure 3:
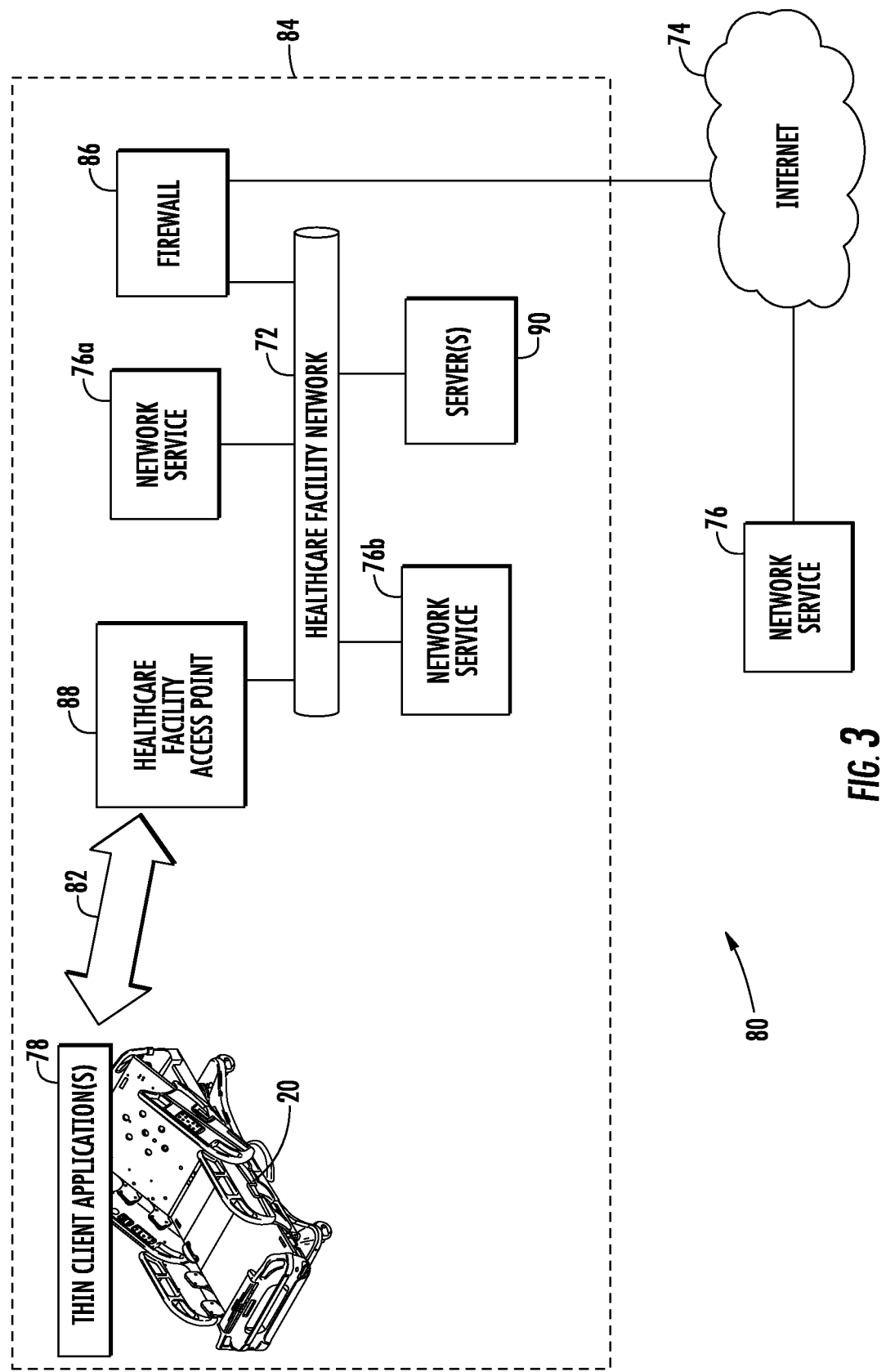
FIG. 3 is a diagram of an illustrative layout of a patient support apparatus communication system.

FIG. 3 illustrates one example of a patient support apparatus software infrastructure layout or configuration 80 that may be implemented by a healthcare facility 84 using one or more patient support apparatuses 20. It will be understood that infrastructure layout 80 is merely an illustrative example of one environment in which patient support apparatus 20 may be implemented, and that various other configurations are possible. Layout 80, however, is provided herein for purposes of explaining various aspects of the invention.

Patient support apparatus software infrastructure layout 80 includes one or more patient support apparatuses 20 that have one or more thin client applications 78 operable thereon. The thin client applications 78 are in electrical communication with one or more network services 76 that are supported on a remote network. The remote network refers to one or more healthcare facility networks 72 positioned within a healthcare facility 84, or one or more networks positioned outside the healthcare facility 84, such as, but not limited to, the Internet 74. It will be understood by those skilled in the art that the term "healthcare facility" will refer not only to an individual building in which patient support apparatuses 20 are positioned, but also collections of buildings (such as are commonly found on a hospital campus). Still further, it will be understood that healthcare facility network 72 refers not only to a Local Area Network that is positioned within a single healthcare facility 84, but also Wide Area Networks that may connect together multiple healthcare facilities 84 that are located in different geographical areas.

Thin client application 78 communicates with the remote network 72 by way of a communications link 82. Communications link 82, in one embodiment, is a wireless communications link that links together transceiver 60 with a wireless access point 88 of the healthcare facility network 72. In one embodiment, communications link 82 is a WiFi communications link and healthcare facility network is an Ethernet. In other embodiments, communications link 82 may be a wired communications link between transceiver 60 and healthcare network 72. Such a wired connection may be carried out by an Ethernet cable, a serial cable, or by other cables. In still other embodiments, communications link is a wireless link that, in some instances, is carried out through the use of one or more mesh networks that patient support apparatuses 20 are part of. Such use of mesh networks to communicate information from patient support apparatuses 20 to a healthcare network, such as network 72, are disclosed in commonly assigned U.S. patent application Ser. No. 13/802,855 filed Mar. 14, 2013 by applicants Michael Hayes et al. and entitled PATIENT SUPPORT APPARATUS COMMUNICATION SYSTEMS, and commonly assigned U.S. Pat. No. 8,461,982 issued to Becker et al. and entitled COMMUNICATION SYSTEM FOR PATIENT HANDLING DEVICES, the complete disclosures of both of which are hereby incorporated herein in their entirety by reference.

As shown in FIG. 3, patient support apparatus 20 runs at least one thin client application 78 that is dependent upon a network service 76 for carrying out one or more of its full functionality. This is not meant to suggest that thin client application 78 must be in communication with network 72 and its associated network service 76 at all times, but rather that communication is at least periodically required for thin client application 78 to carry out all of its designed functionality. As was noted above, the specific thin client application(s) 78, can vary and include, but are not limited to, patient assessment applications, sensor monitoring and/or data collection applications, maintenance monitoring/scheduling applications, billing applications, patient care protocol management applications, and other applications that relate to patient support apparatus 20, or devices in communication with patient support apparatus 20.

The network service 76 that the thin client application 78 interacts with also does not need to be directly coupled to healthcare facility network 72. For some thin client applications 78, the network service 78 may reside outside the healthcare facility 84, such as one that is available through the Internet 74. In order for the thin client application 78 to communicate with such an Internet application 76, the application 78 will typically have to tunnel through a healthcare facility firewall 86 maintained by the IT department of the particular healthcare facility 84 in which the patient support apparatus 20 is located. Because such tunneling may be impeded by firewall 86 (either on the outbound journey and/or the inbound journey), it may be advantageous for certain thin client applications to have their corresponding network service 76 located on the client side of the firewall 86.

Depending upon the specific network service 76 supported on the healthcare facilities network 72, the network service 76 may interact with one or more servers 90 that are also located on, or otherwise accessible by, the network 72. Such servers 90 include, but are not limited to, the following: an electronic medical (EMR) server; an admission, discharge and transfer (ADT) server; a work flow server; a remote alerting server; and/or one or more nurse's station servers. The EMR server typically contains medical information about the particular patient assigned to a particular patient support apparatus 20. The ADT server typically includes information regarding a patient's identification, location, and status within a healthcare facility, and may contain information that enables a network service 76 to determine which patient is presently occupying a particular support apparatus 20, (which can enable the service 76 to know which information is relevant in the EMR server). The work flow server typically contains information identifying health care personnel, including which caregivers are assigned to which patients. One or more network services 76 may access this information to in order to determine which caregivers should be notified of any alerts issued by the patient support apparatus 20, or the thin client application 78. The remote alerting server typically controls alerts that are issued to wireless devices carried by hospital personnel. Such wireless devices include cell phones, WIFI devices, pagers, computer tablets, personal digital assistants (PDAs), or other structures.

Although the aforementioned servers 90 are often found in a typical hospital setting, it will be understood that the specific servers 90 on a particular healthcare facility's network 72 will vary from facility to facility and will depend upon the specific IT system within a given healthcare facility.

In some embodiments, a patient support apparatus 20 will support multiple thin client applications 78 wherein each thin client application 78 communicates with a different network service 76. Thus, for example, in the layout 80 shown in FIG. 3, a first thin client application 78 may interact with a first network service 76a, while a second thin client application 78 running on the same patient support apparatus 20 as the first thin client application 78 will interact with a second network service 76b.

Figure 4:
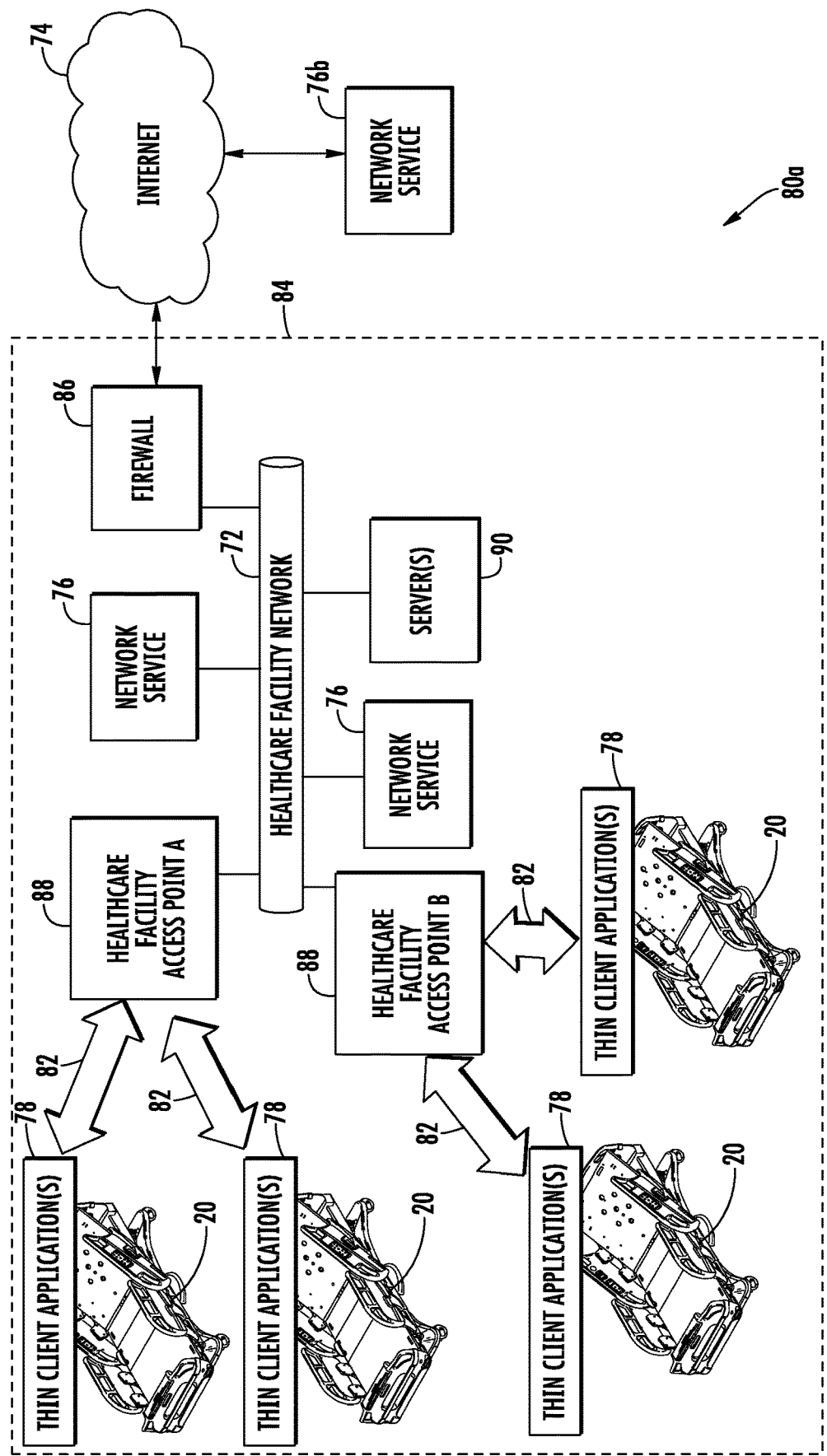
FIG. 4 is a diagram of another illustrative layout of a patient support apparatus communication system showing multiple patient support apparatuses running thin client applications and utilizing multiple access points.

FIG. 4 illustrates another example of a patient support apparatus software infrastructure layout 80a that can be implemented with one or more patient support apparatuses 20 at a healthcare facility 84. Those components that are the same as those found in layout 80 are labeled with the same reference number and operate in the same manner as has been previously described. Those components that are not found in layout 80 are identified with a new reference number.

Layout 80a differs from layout 80 in that layout 80a includes a plurality of patient support apparatuses 20 that are in communication with healthcare facility network 72. Further, layout 80a shows a healthcare facility network 72 having multiple network access points 88. A first set of patient support apparatuses 20 communicate with healthcare network 72 via a first one of the access points 88, while a second set of patient support apparatuses 20 communicate with the healthcare network 72 via a second one of the access points. In many healthcare facilities, there may be more than two access points 88, and a given thin client application 78 on a particular patient support apparatus 20 may communicate with different access points 88 as it moves throughout the healthcare facility 84.

Figure 5:
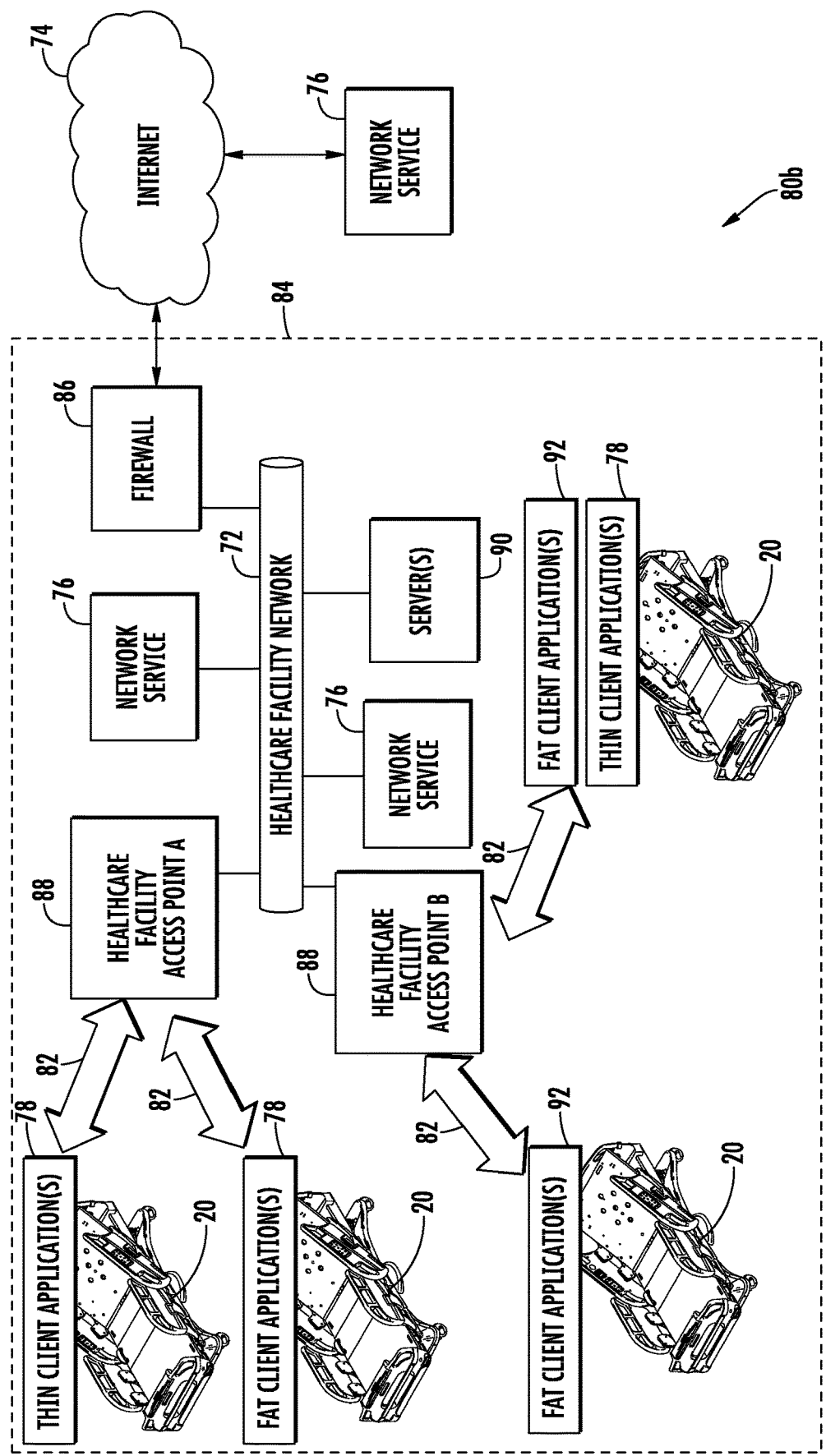
FIG. 5 is yet another diagram of an illustrative layout of a patient support apparatus communication system showing multiple patient support apparatuses running either or both of thin and fat client applications.

FIG. 5 illustrates another example of a patient support apparatus software infrastructure layout 80b that can be implemented with one or more patient support apparatuses 20. In the layout 80b shown in FIG. 5, some patient support apparatuses 20 have thin client applications 78 implemented thereon, while other patient support apparatuses 20 have both thin client applications 78 and one or more fat client applications 92. Still further, at least one patient support apparatus 20 has only a fat client application 92 operating thereon. Fat client applications 92 may be adapted to perform any of the potential functions described above that can be performed by thin client applications 78 (e.g. patient assessment applications, sensors monitoring and/or data collection algorithms, maintenance monitoring/scheduling applications, billing applications, patient care protocol management application). The only difference between thin client applications 78 and fat client applications 92 is that fat client applications 92 rely more heavily on the local controller 52 for carrying out their functions, and less on the network service 76 than do thin client applications 78. That is, while fat client applications 92 still rely on at least periodic access to network service 76 to perform their full functionality, fat client applications 92 are able to perform more functions in the absence of the connection to the network service 76 than a thin client application 78.

Figure 6:
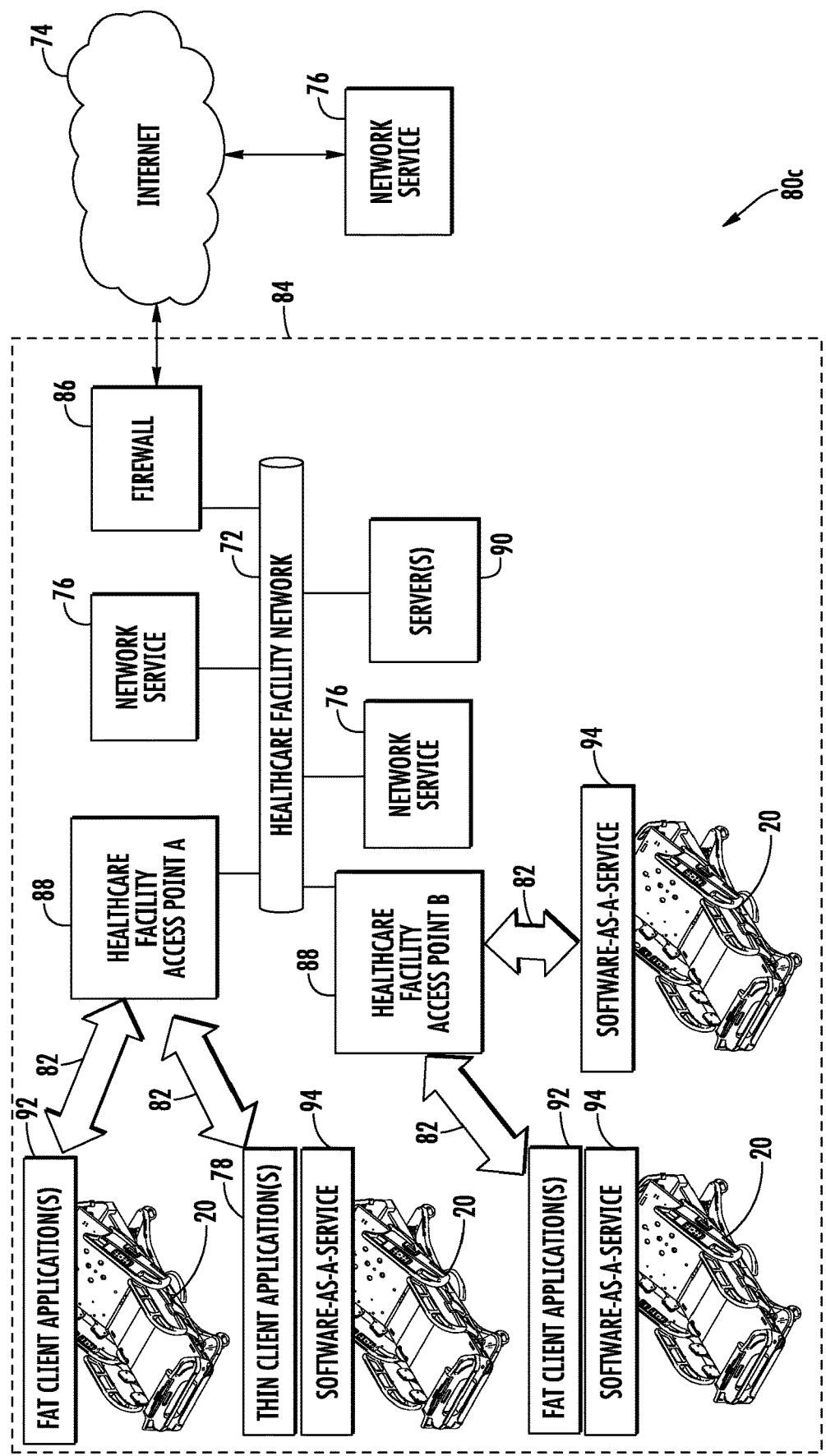
FIG. 6 is still another diagram of an illustrative layout of a patient support apparatus communication system showing multiple patient support apparatuses running any one or more of thin client, fat client, and Software-as-a-Service applications.

FIG. 6 illustrates yet another example of a patient support apparatus software infrastructure layout 80c that can be implemented with one or more patient support apparatuses 20. As with layouts 80, 80a, and 80b, those components that are the same as those found in layouts 80, 80a, or 80b are labeled with the same reference number and operate in the same manner as has been previously described. Those components that are not found in layouts 80, 80a, or 80b are identified with a new reference number.

Layout 80c differs from layouts 80, 80a, and 80b in that at least one patient support apparatus 20 is included within the healthcare facility 84 that is operating a Software-as-a-Service application 94. The Software-as-a-Service (SaaS) applications 94 differ from the thin client applications 78 and the fat client applications 92 in that the network service 76 which interacts with the SaaS application 94 is hosted by an entity other than the healthcare facility. That is, although the SaaS application 94 may utilize a thin or fat client architecture to carry out its functions, the network service 76 will typically be hosted by a company that is not the hospital, or healthcare institution, that owns or operates facility 84. In many cases, although not all cases, the SaaS application will therefore interact with a network service 76 that is located on the service side of the firewall 86. In some embodiments, the network service 76 that interacts with the SaaS application 94 is hosted by the company that manufacturers patient support apparatus 20, or a company that has contracted with the manufacturer of the patient support apparatus 20.

As shown in the example of FIG. 6, some patient support apparatuses 20 are only operating a SaaS application 94, while other patient support apparatuses 20 are operating a SaaS application in addition to other applications, such as a thin client application 78 or a fat client application 92. Still other patient support apparatuses 20 are operating one or more thin or thick client applications 78 or 92 without operating any SaaS applications. The SaaS applications 94 may carry out any of the functions described above that can be performed by the thin or fat client applications (e.g. patient assessment applications, sensors monitoring and/or data collection algorithms, maintenance monitoring/scheduling applications, billing applications, patient care protocol management application).

It will be understood by those skilled in that art that, although FIGS. 4-6 show patient support apparatuses 20 as all being identical to each other, this does not need to be the case. Different types of patient support apparatuses 20 may be used within a given facility 84. For example, as was noted previously, patient support apparatuses 20 include, but are not limited to cots, beds, stretchers, recliners, and/or operating tables. Thus, in the layouts of FIGS. 4-6, it is to be understood that references to patient support apparatus 20 are meant to include any of these types of patient support apparatuses, and that a mix of such support apparatuses may be included in any of layouts 80a, 80b, and 80c. Further, it will also be understood that different versions of thin client applications 78 may operate for different types of patient support apparatuses 20. Still further, in some layouts, completely different thin client applications may be available for different types of patient support apparatuses. In other words, an operating table might use a different application 78 than a bed, while a stretcher might use a thin client application 78 that is different from those that operate on a bed. Similar variations are possible for both fat client applications 92 and SaaS applications 94. Other variations are also possible.

Figure 7:
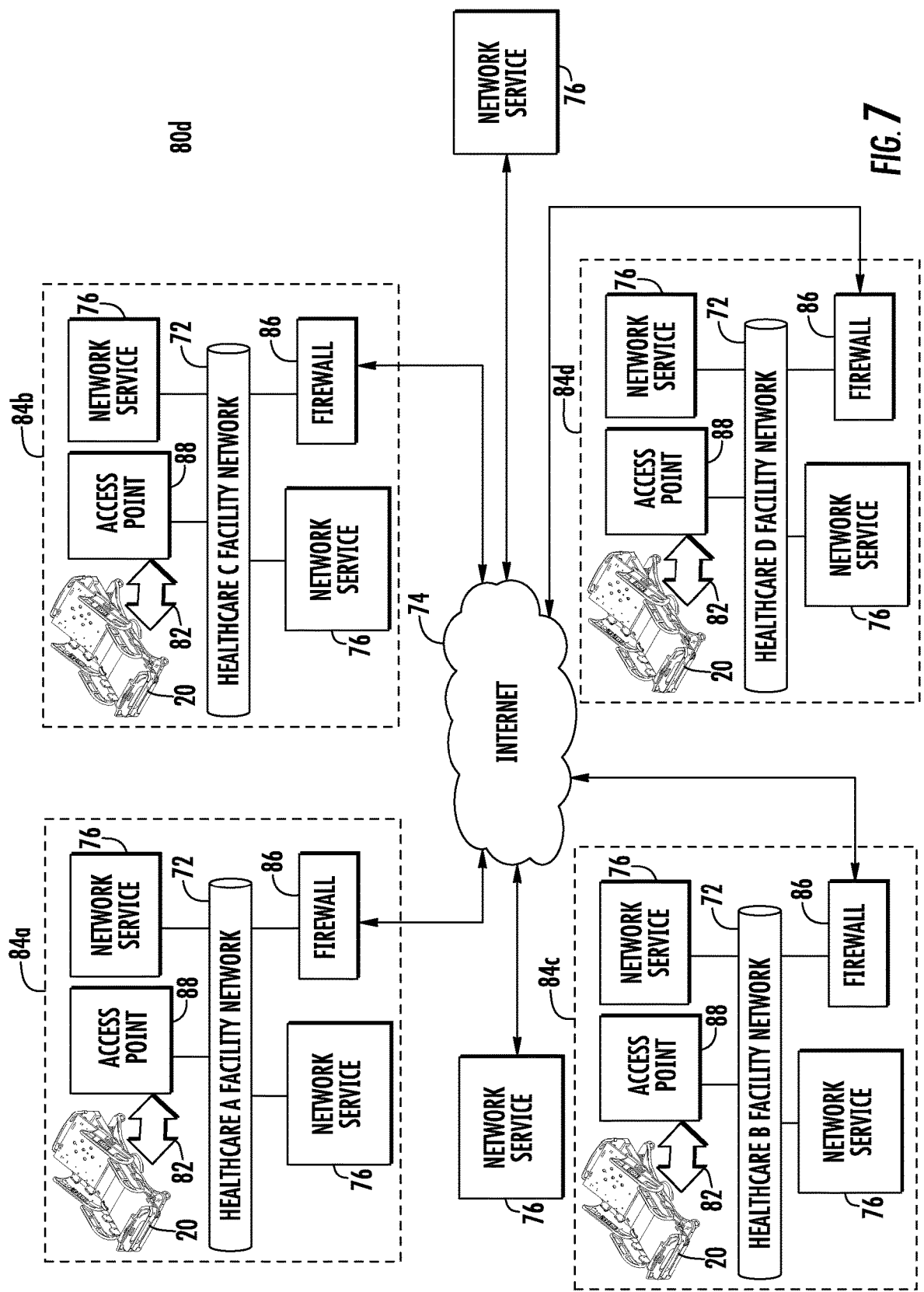
FIG. 7 is another diagram of an illustrative layout of a patient support apparatus communication system that includes multiple healthcare facilities.

FIG. 7 illustrates yet another patient support software infrastructure layout 80d that can be implemented with one or more patient support apparatuses 20. As with layouts 80, 80a, 80b, and 80c, those components in layout 80d that are the same as those found in the previously described layouts are labeled with the same reference number and operate in the same manner as has been previously described. Those components that are not found in layouts 80, 80a, 80b, or 80c are identified with a new reference number.

FIG. 7 differs from the previously described layouts 80 in that it includes multiple healthcare facilities 84 (84a, 84b, 84c, and 84d). FIG. 7 also differs from the previously described layouts 80 in that specific type of software applications (e.g. thin client, fat client, and/or SaaS) implemented on the various patient support apparatuses 20 are not identified. This lack of identification is intended to show that any of these three types of software applications may be implemented on any of these patient support apparatus, including any combinations and/or permutations of these types of software. Further, not only can the software applications on one or more patient support apparatuses 20 within a given healthcare facility 84 vary between the patient support apparatuses 20 within that facility, they can also vary from facility to facility.

Although the software infrastructure layout 80d of FIG. 7 only shows four healthcare facilities connected to the network service 76 that is accessible via the Internet 74, it will be understood that this is only an arbitrary example provided for purposes of illustration. Further, while each facility 84 only shows a single patient support apparatus 20 and a single access point 88, this number will vary from facility 84 to 84. Still further, although FIG. 7 shows each healthcare facility having two local network services 76, this number can also vary in different facilities 84. Finally, although FIG. 7 illustrates each healthcare facility 84 as lacking any servers 90, it will be understood that this omission is merely for purposes of space saving convenience, and that healthcare facilities 84 will typically include one or more servers 90 on their local networks 72.

Infrastructure layout 80d is especially useful for software applications (thin, fat, or SaaS) that gather data from patient support apparatuses 20 across multiple healthcare institutions and use the data for billing purposes (e.g. patient support apparatus 20 usage data), for carrying out population studies, for evaluating compliance with patient care protocols that have patient support apparatus-related components, for ensuring that the patient support apparatuses 20 are properly maintained, and for other purposes, a number of which will be discussed in greater detail below. This list of potential uses, however, is not meant to suggest that these types of applications cannot also, or alternatively, be carried out using a local network service 76 (i.e. one on the network 72 inside the respective firewall 86).

Figure 8:
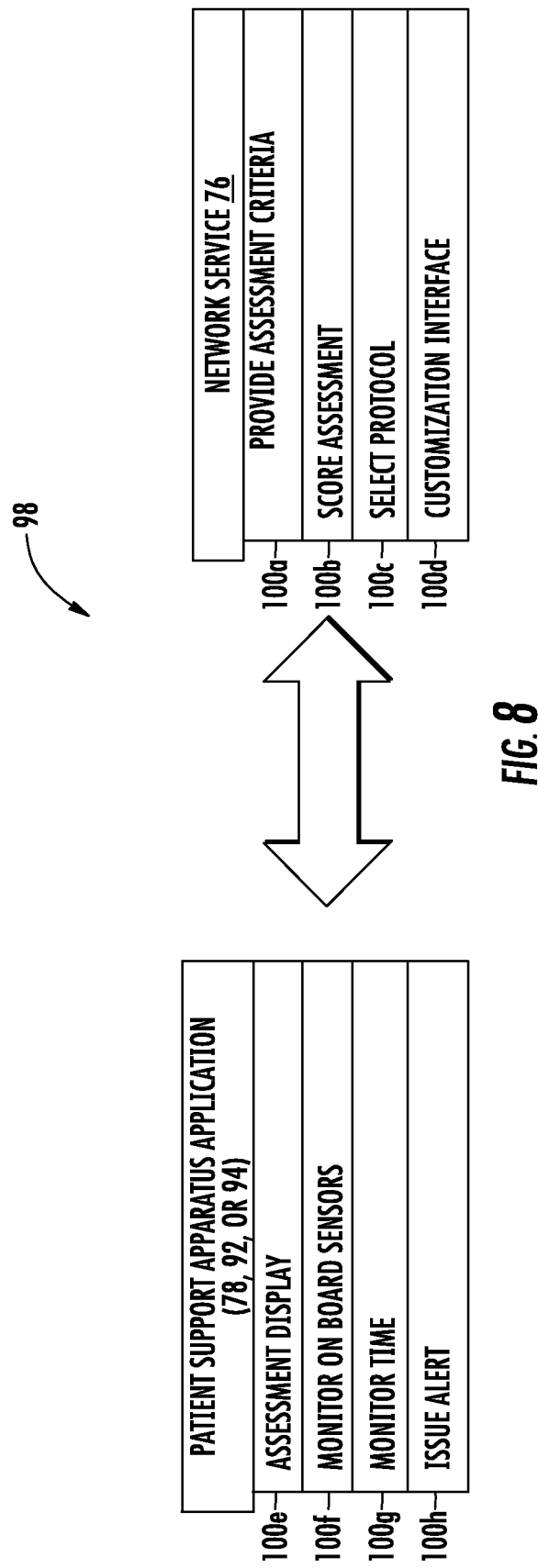
FIG. 8 is a diagram of an illustrative architecture of an assessment software application that may be used with any of the communication systems and patient support apparatuses described herein.

FIG. 8 illustrates one potential arrangement of a patient assessment software application 98 that operates both on patient support apparatus 20 and network service 76. The application 98 shown in FIG. 8 can be a thin client application 78, a fat client application 92, or a SaaS application 94. It will be understood that the particular arrangement shown in FIG. 8 is merely an illustrative example of the types of applications that may operate on patient support apparatus 20 and interact with one or more network services 76, and that modifications to the arrangement shown therein can be made such that some functions carried out by the patient support apparatus 20 are carried out by the network service 76, and vice versa. Further, it will be understood that, although application 98 relates to software used in assessing an aspect of a patient's health, the principles discussed below in regard to this application 98 can be applied to any of the other types of applications discussed herein.

The patient assessment software application 98 of FIG. 8 is specifically designed for assessing a patient's risk of developing bed sores and implementing a patient care protocol based on that assessment. The application 98 includes a plurality of features or functions 100. FIG. 8 illustrates where portions of the software that carry out each of these functions or features 100 reside, or more specifically, where the computations necessary for carrying out each of these functions or features 100 take place. As shown, patient assessment application 98 includes four features or functions 100a, 100b, 100c, and 100d that are computationally performed by the network service 76, and another four features 100e, 100f, 100g, and 100h that are computationally performed by controller 52 on patient support apparatus 20. The results of these computations are shared between controller 52 and network service 76, as needed, using communication link 82.

Patient assessment software application 98 includes an assessment display function 100e that is performed by controller 52 at patient support apparatus 20. Display function 100e carries out the display of any and all information that is necessary for performing the functions of assessment application 98. In the patient support apparatus 20 shown in FIG. 2, controller 52 carries out the display function 100e by controlling the information displayed on display 66, which is located in the footboard 32 of patient support apparatus 20. More specifically, controller 52 carries out display function 100e by controlling the display of any icons, menus, graphics, or other user interface items on display 66 that are used in the patient assessment software application. The content and/or definition of the items displayed by controller 52 on display 66 may be dictated in whole or in part by network service 76, as will be discussed below.

Assessment criteria function 100a (FIG. 8) of patient assessment application 98 is carried out by network service 76. The assessment criteria function 100a refers to the selection and/or definition of what criteria are going to be used in the patient assessment. As one example, the assessment criteria function may refer to using the Braden scale for assessing a patient's risk of developing bed sores. If this is the criteria, then the corresponding network service 76 stores the questions and contents of the Braden scale assessment. If a different method for assessing the bed sore risk is used—such as a modified Braden scale assessment, or a completely different assessment—then assessment criteria function 100a stores this modified or different assessment. In many instances, the assessment will include, but not necessarily be limited to, a list of questions that a caregiver is required to answer about a patient. With respect to the Braden scale, these questions relate to the patient's sensory perception, skin moisture, patient activity, patient mobility, nutrition, and friction and shear. Such question may differ if a different assessment is used. However, whatever assessment is used, the definition and contents of that assessment are stored at network service 76.

When a caregiver begins the assessment application 98, controller 52 may already have a local copy of the assessment criteria function 100a stored at network service 76 by way of a previous communication with network service 76 via link 82. However, in at least one embodiment, application 98 is configured, upon startup, to contact network service 76, if it is currently available, and either to download the latest version of the assessment criteria function 100a, or to confirm that the controller 52 at the patient support apparatus has the latest assessment criteria function 100a stored locally in memory 54. If network service 76 is unavailable at the time of startup of application 98, then controller 52 will, in some embodiments, issue an alert on display 66 indicating that the network service 76 is currently unavailable, and ask the caregiver if he or she would like to continue using the local copy of the assessment criteria function 100a. Regardless of whether the caregiver selects to continue or not, application 98 will continue to make attempts at contacting network service 76 until communication is established, at which point controller 52 will indicate this successful communication on display 66.

Network service 76 also stores the data which defines how an assessment is scored at feature 100b. That is, while function 100a defines the questions and criteria that are used to assess the patient, function 100b defines the manner in which the answers to the questions of function 100a are converted into a numeric score, or, in some cases, a qualitative score. For example, the Braden scale customarily converts the various assessment questions into a score that ranges from 6 to 23, where a score of 23 represents the lowest risk of developing bed sores, while a score of 6 represents the highest score of developing bed sores. Scoring feature 100b therefore contains the intelligence necessary for performing this scoring, or a modified version of this scoring, which a hospital administrator can implement using the customization interface 100d, as will be discussed in greater detail below.

The protocol selection feature 100c is also stored on network service 76 and determines the patient care protocol that should be followed in light of the score that resulted from the analysis carried out by feature 100b. In other words, feature 100c, using the example of the Braden scale again, determines what patient care protocol should be followed for each of the seventeen different numeric Braden scale scores. In many instances, the intelligence of the protocol selection feature 100c will group the scores into ranges, and any scores in a particular range will result in the same patient care protocol being recommended, while scores in a different range will result in either a different patient care protocol, or no patient care protocol.

As an illustrative example, if a particular patient scores a 10 on the Braden scale, the data stored at network service 76 for feature 100c will be used by network service 76 to select a particular patient care protocol that helps to reduce the likelihood of a patient developing bed sores. The definition of the patient care protocol can vary, but in one embodiment includes—among potentially other features—a definition of how often a patient should be turned. In some instances, a higher risk of bed sores for a particular patient will generally correspond to a higher frequency of patient turns, although not all assessment programs 98 need to be implemented in this manner. In other embodiments, the patient care protocol may specify certain characteristics or settings of the mattress 36 supported on patient support apparatus 20. For example, the protocol might specify that a low air loss feature on the mattress be turned on in order to help reduce moisture build up, which is correlated with increased likelihood of bed sores. The patient care protocol might also specify an inflation pressure for one or more of the inflatable bladders inside of the mattress. In still other embodiments, the patient care protocol might specify one or more mattresses, or types of mattresses, that need to be used with this particular patient (and if they are not present on the patient support apparatus 20, a caregiver will be required by the protocol to change the mattress to match the protocol). Still other aspects and definitions of the patient care protocol may also be contained within the protocol select feature 100c.

After a particular patient care protocol has been selected using the selection feature 100c, patient support apparatus 20 is ready to implement those portions of the patient care protocol that relate to patient support apparatus 20, or mattress 36, or any other feature or device that is in communication with patient support apparatus 20. In some embodiments, the patient care protocol selected by feature 100c will require the monitoring of one or more sensors on board patient support apparatus 20, such as, but not limited to, force sensors 62. This is performed locally by controller 52 and carried out as part of function 100f. Further, in some patient care protocols, the passage of time needs to be measured, such as, for example, the time since a patient was last turned. This monitoring of time is also carried out locally in application 98 via function 100g. Application 98 also includes an alerting feature that is carried out whenever application 98 determines that the patient care protocol isn't being followed, or the protocol requires some action by the caregiver. For example, if the patient care protocol requires that a patient be turned every two hours, application 98 will issue an alert after the passage of two hours without the patient being turned. The alert can be a local alert, a remote alert, or both. If local, it can involve a message displayed on display 66, or an aural sound, or the illumination or flashing of one or more lights. If remote, controller 52 forwards the alert via transceiver 60 to the appropriate destination on network 72 for transmitting the alert to the desired caregivers (e.g. to a remote alerting server 90 discussed above).

As another example, an alert may be issued by application 98 if the patient care protocol specifies that a specific mattress be used with patient support apparatus 20 and controller 52 does not detect the appropriate mattress type (via interface 58), or if the patient care protocol specifies that a low air loss feature of the mattress 36 be turned on, and this is not turned on (as controller 52 would detect via interface 58). In general, any parameters of the patient care protocol that controller 52 is capable of confirming or analyzing will generate an alert if the confirmation is negative, or if the analysis leads to a result calling for caregiver attention.

While it was briefly mentioned above, it bears repeating that the particular division of functions 100 of application 98 shown in FIG. 8 can be varied. That is, in some embodiments of assessment application 98, any of functions 100f, 100g, and/or 100h might also be performed via network service 76. Indeed, in some embodiments, even the control of the screen space of display 66 of feature 100e could be carried out by way of network service 76. Alternatively, any one or more of the features or functions 100a, 100b, 100c, and/or 100d could be carried out locally by controller 52 on patient support apparatus 20. In some embodiments, controller 52 will retain in memory 54 a local copy of all of the data and instructions associated with the features or functions 100a, b, c, and d that are carried out by assessment application 98 and utilize that local copy if communications link 82 is broken, or if controller 52 is otherwise unable to communicate with service 76. However, when service 76 is available, application 98 will use the network service 76 to perform, rather than the local copy. In still other embodiments, controller 52 may not have a local copy of any of the features 100 of network service 76, in which case, if the service is temporarily unavailable, then the application 98 will not operate correctly.

While not required for assessment application 98 to operate properly, the particular embodiment of assessment application 98 shown in FIG. 8 also includes a customization interface 100d that is configured to operate via network service 76. Customization interface 100d is adapted to allow authorized personnel at the particular healthcare institution to change any of the data or instructions associated with any of the network features or functions 100a, 100b, and/or 100c. This allows a healthcare facility to easily implement their own custom patient care protocols, their own criteria for determining when such protocols are to be used, and/or their own criteria for interpreting the results of their custom assessments. In other words, customization interface 100d allows authorized personnel to change what bed sore assessment will be used by network service 76 (e.g. a healthcare institution could change from using the Braden scale to another criteria). It also allows authorized personnel to change how the results of the assessment questions are scored (feature 100b). Still further, it allows authorized personnel to change which protocols correspond to which scores, and how those protocols are defined (feature 100c).

Customization interface 100d therefore provides users with greater flexibility for carrying out patient care in a manner that reflects the judgment and opinions of the particular healthcare institution that is running application 98. This flexibility is not present in prior art patient support apparatuses where, when they include features regarding patient care protocols, they are hard coded into the patient support apparatus itself and cannot be easily changed. Further, this flexibility allows a healthcare institution at least several advantages over prior art patient support apparatuses.

First, this flexibility allows a healthcare institution to easily change their patient care protocols as medical research and health information is developed and discovered. For example, if a new medical study is published indicating that reducing bed sores for patient's having a Braden scale score of 10 requires a patient to remain immobile for no longer than X minutes, then the healthcare institution can update their patient care protocol to require patient turns every X minutes, or some other time period based upon the published research. Alternatively, if medical research shows that the Braden scale is not as accurate as another measurement of bed sore risk, then the medical institution can switch function 100a to include the questions, data, and other information for that different measurement.

Second, this flexibility allows a healthcare institution to more easily monitor the effectiveness of its patient care protocols. For example, an evaluation feature can be added to application 98, or another separate application can be implemented, that records the actual steps taken by the caregiver, including when patient turns are implemented, how much time passes between turn intervals, what mattresses are used, what mattress setting were used with a patient, etc. This information is gathered for all patient support apparatuses 20 within the healthcare institution and stored in a central location. Further, this information can then be easily compared to an EMR database, or other database, that contains the actual history of bed sore developments for patients in that healthcare facility. By appropriately correlating the sensor data gathered from the patient support apparatuses 20 with the clinical records of the patients that have been supported thereon, the effectiveness of the patient care protocol can be evaluated. In other words, if it turns out that patients with a particular bed sore risk score are still developing bed sores with a patient care protocol X, then the healthcare facility can easily use customization interface 100d to change the patient care protocol corresponding to that bed sore risk score. Other modifications can also be made, depending upon the outcome of the correlation analysis.

As was noted above, in some embodiments of assessment application 98, application 98 carries out the monitoring function 100g by monitoring the outputs of one or more sensors, such as, but not limited to, force sensors 62. It will be understood that the precise nature of the monitoring, as well as the sensors monitored, will vary from application to application. In one embodiment, assessment application 98 continuously, or nearly continuously, monitors the outputs of force sensors 62 and keeps track of the amount of movement of the patient supported on patient support surface 28. Further, controller 52 carries out function 100g by monitoring the outputs of forces sensors 62, and/or other sensors, to determine when a patient has turned, whether on his or her own, or with the help of a caregiver. Controller 52 may also monitor still other sensors on board patient support apparatus 20, such as, but not limited to, one or more vital sign sensors, a patient pressure interface mat positioned on top of—or integrated into—the mattress, or still other sensors. The manners in which these sensors can be monitored for determining such things as patient turning, patient movement levels, vital signs, and other information can be accomplished in a variety of different manners, some of which are disclosed in commonly assigned U.S. patent application Ser. No. 61/791,117, filed Mar. 15, 2013, by Michael Hayes et al. and entitled PATIENT SUPPORT APPARATUS WITH PATIENT INFORMATION SENSORS; Ser. No. 61/881,581 filed Sep. 24, 2013 by applicants Joshua Mix et al. and entitled PATIENT SUPPORT APPARATUS; and Ser. No. 61/932,574 filed Jan. 28, 2014 by applicant Annie Desaulniers and entitled SYSTEM AND METHODS OF MANAGING AURAL AND/OR VISUAL INDICATIONS; the complete disclosures of all of which are hereby incorporated herein by reference.

In addition to, or in lieu of patient assessment application 98, a variety of different applications can operate as a thin client application 78, or a fat client application 92, or a SaaS application 94 on patient support apparatus 20. While the following list and description of some examples of such applications are provided, this list is not meant to be exhaustive, and other applications and/or modifications to these applications can be made.

Another patient assessment application that can operate on patient support apparatus 20 (as a thin client, fat client, or SaaS application), is a fall risk patient assessment application. Such a fall risk assessment application operates similar to the bed sore assessment application 98 except it is modified to address the potential of a patient falling, rather than the potential of a patient developing bed sores. Such an application includes one or more features that are comparable to bed sore assessment application 98, such as: (1) a list of criteria or questions to be answered in a manner similar to function 100*a* of application 98; (2) an algorithm or other intelligence for scoring the results of the questions, similar to feature 100*b* of application 98; (3) a selection and definition of a fall prevention patient care protocol that will be used in response to the assessed score (similar to feature 100*c* of application 98); (4) and a plurality of features that monitor sensors and/or time, and that issue necessary alerts (similar to features 100*f,* 100*g,* and 100*h* of application 98). Such fall prevention protocols will typically include one or more of the following requirements: the brake on the patient support apparatus is set; the height of the frame 26 is at its lowest height, or at least less than a threshold height; the side rails 46 are positioned in an up position, and a patient exit alert system is activated. The protocol also specifies, in some embodiments, a specific setting for the patient exit alert system (for those patient support apparatuses that have different thresholds for triggering the patient exit alert).

Another application that can operate on patient support apparatus 20 as a thin client, fat client, or SaaS application is a ventilator patient care protocol application. Such a ventilator patient care protocol specifies what steps a caregiver is supposed to take with respect to patient support apparatus 20 (and/or mattress 36) when a patient using the patient support apparatus 20 is connected to, or about to be connected to, a ventilator. While the specific patient care protocol can vary, one protocol will customarily require that the angle of the Fowler section of the patient's bed be maintained above a certain threshold angle, such as thirty degrees. By keeping the patient's torso in an upright position, the likelihood of ventilator associated pneumonia (VAP) is reduced. The ventilator application therefore instructs the caregiver to configure the patient support apparatus in such an upright position and, if the patient support apparatus is so equipped, activate a lockout feature that prevents the patient support apparatus from being moved to an angular position less than the threshold. In some embodiments, the ventilator application can prescribe an angular orientation of the Fowler portion of the bed that can be customized for a particular healthcare institution via a customization interface (similar to customization interface 100*d* of application 98). In still other embodiments, the ventilator application can be configured to run automatically when the patient support apparatus detects the presence of a nearby ventilator via near field communication. Such detection can be carried out in any of the manner disclosed in the commonly assigned U.S. patent application Ser. No. 13/802, 992, filed Mar. 14, 2013 by applicants Michael Hayes et al, and entitled COMMUNICATION SYSTEMS FOR PATIENT SUPPORT APPARATUSES, the complete disclosure of which has already been incorporated herein by reference.

The ventilator protocol application may also include a customization interface, similar to customization interface feature 100*d* of application 98. This customization interface allows the ventilator protocol to be modified in accordance by authorized healthcare administrators. Such customization allows the administrator to sets the minimum threshold angle of the Fowler section of the patient support apparatus which is not to be broken during the implementation of the ventilator protocol. Other customizations are also possible.

Another application that can operate on patient support apparatus 20 as a thin client, fat client, or SaaS application is a compliance monitoring application similar to that described above. Such a compliance monitoring application monitors how well any of the various patient care protocols (including, but not limited to, the bed sore prevention and fall prevention protocols mentioned above) are followed. Such a compliance application monitors and records the outputs from all of the sensors on the patient support apparatus that output information that can be used to determine whether any aspect of the patient care protocol has been followed or not. As an example, if a fall prevention protocol is implemented that requires the side rails 46 on the patient support apparatus 20 to be maintained in an up position, sensors (not shown) on patient support apparatus 20 will forward their outputs to controller 52 which will record these and forward them onto the network service 76. The time at which a side rail goes out of compliance is recorded, as well as the total duration of time that the side rail is out of compliance. Network service 76 makes this information available to the healthcare institution so that administrators can gauge how effectively their protocols are being followed.

As another example, a compliance application can be used to monitor compliance with patient care protocols used for preventing ventilator associated pneumonia (VAP). As discussed, such protocols typically require that the Fowler portion of a bed (e.g. head section 38 of patient support apparatus 20) be maintained at an angle above thirty degrees, or some other threshold. Controller 52 communicates with a sensor (not shown) that measures the angle of the Fowler portion on patient support apparatus 20 and—when carrying out the compliance application—records the outputs from this sensor and forwards them to the compliance network service.

One or more billing applications can operate on patient support apparatus 20 (as thin client, fat client, or SaaS applications) that record the amount of time a patient is in patient support apparatus 20, as well as the amount of usage of certain features on the patient support apparatus 20 which are used with a particular patient. This information is forwarded by the application to the corresponding network service 76 where it is made available to the healthcare administrators who can use it to bill patients based on the amount of time and/or usage of patient support apparatus 20, and/or any of the individual features of patient support apparatus 20.

One or more maintenance applications can also, or alternatively, operate on patient support apparatus 20 as thin client, fat client, and/or SaaS applications. In one embodiment, a maintenance application operates on patient support apparatus 20 that counts the number of times each of the various actuators 68 on board patient support apparatus 20 are used. These actuators include the tilt actuator 68*a,* deck actuator(s) 68*b,* lift actuator(s) 68*c,* and/or brake actuator(s) 68*d.* The maintenance application records the counts for each of the individual actuators and compares these counts to thresholds corresponding to each of these various actuators. If any of the counts exceed the corresponding threshold, a maintenance alert is issued (either locally, remotely, or both) by the maintenance application. Preventative maintenance can then be performed on the patient support apparatus based upon the device's actual usage, rather than a simple passage of time (which may or may not reflect use conditions). The maintenance application therefore helps ensure that patient support apparatuses 20 receive the proper care in a timely manner.

In addition to counting the physical movement of various components of patient support apparatus 20, the maintenance application can also keep track of the number of times one or more rechargeable batteries on the patient support apparatus 20 are charged and discharged. Further, the extent of the discharging and recharging can be monitored and recorded. This information is then transmitted to network service 76 which uses the information to determine when the rechargeable batteries should be replaced. This helps ensure that the rechargeable batteries are replaced on a timely basis, but not unnecessarily often.

The maintenance application can also, in some embodiments, gather and store the usage data for comparison with a database containing actual failures or component breakdowns. In such embodiments, the data gathered from the maintenance application is compared to the database of component failures and modifications to the maintenance schedule can be adjusted, if necessary, based on the results of the comparison. Still further, mean times between failures (MTBF) of components in actual field use can be calculated, and this information can be used to set schedules and/or thresholds for preventive replacements of components prior to their breaking down so as to minimize down time.

Another type of application that can also, or alternatively, operate on patient support apparatus 20 as a thin client, fat client, and/or SaaS application is a data-gathering and analysis application. The data gathering refers to the gathering of any and/or all sensor information that the patient support apparatus is capable of generating. This information is forwarded by the application to a network service 76 (whether inside firewall 86 or outside firewall 86) that stores the data and allows population studies on large numbers of patient support apparatuses 20 to be performed. The types of studies are customizable according to the interests of the manufacturer of the patient support apparatus 20, or according to the interests of one or more healthcare facilities. Such studies might include, for example, studies that look for correlations between patient movement on support surface 28 (as measured by force sensors 68) and the subsequent exiting of the patient from the patient support apparatus 20. Such studies may be capable of finding patterns between certain movements and the subsequent exiting of a patient from the support surface 28. By finding such patterns, it will be possible to design an exit alert system application that can issue exit alerts a greater amount of time ahead of the patient's exit than existing alert systems. By issuing such alerts further in advance of patient exit, a caregiver is given more time to come to the room the patient is in and assist him or her from exiting from the support apparatus 20, thereby reducing the risk of a patient fall. Other types of studies may also be carried out using such data gathering applications.

Yet another type of application that can also, or alternatively, operate on patient support apparatus 20 as a thin client, fat client, and/or SaaS application is an infection control application. The infection control application monitors what equipment is associated with patient support apparatus 20 and maintains a log of this equipment so that, if a contagious infection is later detected, the equipment associated with that patient can be easily identified and sanitized. The determination of what equipment is associated with a particular patient and/or patient support apparatus 20 can be carried out in any of the manners disclosed in the aforementioned commonly assigned U.S. patent application Ser. No. 13/802,992.

Still another type of application that can be added to patient support apparatus 20 is a video application that makes videos available for display on display 66 of patient support apparatus 20. Such videos may be videos that explain how to operate one or more features of patient support apparatus 20. Alternatively, or in addition, such videos may be videos that explain how to service, troubleshoot, or repair any aspects of patient support apparatus 20. Still further, such videos could include information for caregivers about any of the various patient care protocols mentioned above. The content of such videos, however, would be stored remotely, e.g. at the network service 76, in order to reduce the memory burden on board patient support apparatus 20, as well as to allow the contents of such videos to be more easily changed or updated.

Any of the foregoing applications that can operate on patient support apparatus 20 may also include a customization interface feature similar to feature 100d. Such a customization feature allows healthcare institutions to modify the corresponding application to meet their particular needs. Such customization gives the healthcare facility greater flexibility in billing, maintenance, patient care, data collection, and compliance monitoring.

From the foregoing description, it should be clear that control system 50 of patient support apparatus 20 is configured in a manner that is generally similar to current smart phones which can support one or more apps where the apps carry out functions and/or computations that are not all done locally at the smart phone. Instead, such apps typically interact with network services that are available via a 3G, 4G, or WiFi connection to the Internet, although such interaction is generally invisible to the user of the app. In a similar manner, control system 50 is adapted to support the addition of thin, fat, or SaaS patient support apps (applications 78, 92, and/or 94) that can be added to and removed from patient support apparatus 20 and that interact with remote network services 76, wherein such interaction is generally invisible to the caregiver, or other operator, of the patient support apparatus 20. Further, just as with a smart phone app, some of the algorithms used by these patient support apps are defined by the remote network service and can be varied by the remote network service in a manner that is invisible to the user.

Still further, patient support apparatuses 20 are adapted to be able to have new patient support apps installed without requiring a person to physically connect a memory device containing the new app to the patient support apparatus. Instead, control system 50 is configured to automatically search for available patient support apps and display the available apps on display 66. This enables the appropriate personnel at the healthcare facility to download the desired patient support apps to the patient support apparatus by simply choosing the desired patient support apps. If proper authorization is provided, and/or proper payment arrangements are made, the desired apps are automatically downloaded to control system 50 via communications link 82.

Control system 50 is also adapted to support patient support apps that provide new features on the patient support apparatus 20. For example, some patient support apparatuses 20 may be sold to customers with a patient scale system (e.g. a set of force sensors 62 that are able to determine patient weight), but no patient exit detection system. If the customer later desires to add a patient exit detection systems, the customer can download a patient support app (after establishing proper authorization and making the appropriate payment arrangement) that utilizes the existing scale system to implement a patient exit detection system. For example, the patient exit detection system app can utilize the outputs of the force sensors 62 to calculate the center of gravity of a patient positioned on the patient support surface 28 and issue an alert if the patient's center of gravity moves outside of a selected zone. One manner in which these center of gravity and alerting functions may be carried out is disclosed in commonly assigned U.S. Pat. No. 5,276,432 issued to Travis and entitled PATIENT EXIT DETECTION MECHANISM FOR HOSPITAL BED, the complete disclosure of which is also hereby incorporated herein by reference.

Figure 9:
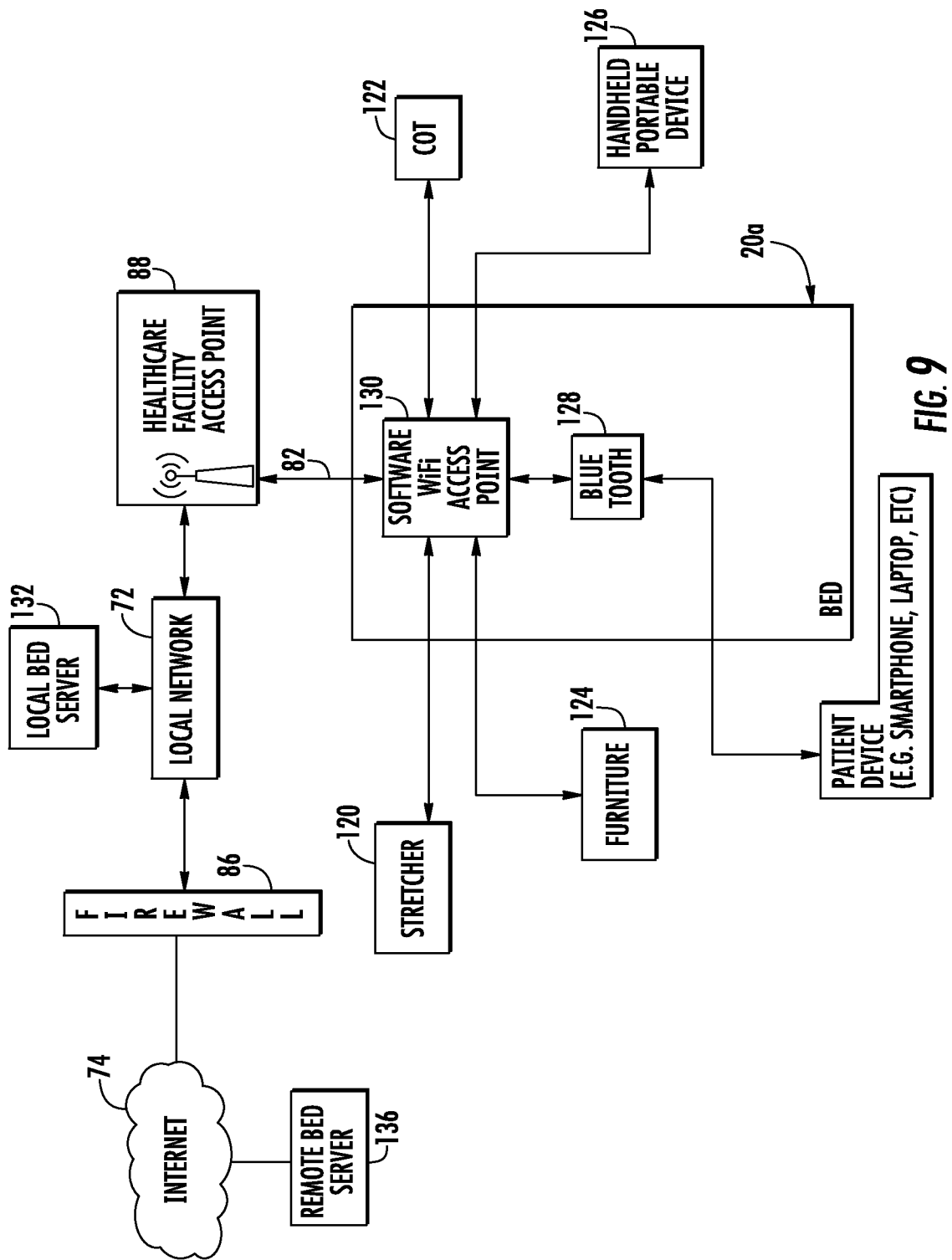
FIG. 9 is a diagram of a patient support apparatus incorporating a wireless hot spot communication feature according to another embodiment of the present invention.

FIG. 9 illustrates another patient support apparatus 20a according to another embodiment of the present invention. Patient support apparatus 20a may or may not include a control system that allows for patient support apps to be downloaded thereto. Indeed, in one embodiment, patient support apparatus 20a includes purely local software that controls the functions of patient support apparatus. In other embodiments, patient support apparatus 20a may have the ability to support thin client, fat client, and/or SaaS applications, as patient support apparatus 20 does. However, regardless of whether the software on patient support apparatus 20a operates only locally, or both locally and remotely, patient support apparatus 20a includes electronic circuitry and programming that create a software wireless access point 130. Software wireless access point 130 is connected by a wireless WiFi connection to any one or more of the wireless access points 88 within the corresponding healthcare facility. Wireless access point 88 is, as noted above, electrically coupled to healthcare communications network 72, and, in some cases, the Internet 74 and any network services 76 that are hosted outside the healthcare facility 84, as well as in the illustrated embodiment, a remote bed server 136.

Software wireless access point 130 provides a mechanism for any of a variety of different devices to communicate with network 72, including any servers that are installed thereon by the healthcare facility, as well as with the Internet 74, and resources or servers in communication with the Internet 74. In the embodiment shown in FIG. 9, a local bed server 132 is shown configured on the local network 72, while a remote bed server 136 is shown configured for Internet communications. In some embodiments, one or both of these servers 132 and/or 136 may be omitted. When included, local bed server 132 functions to receive data transmitted by patient support apparatus 20a (which is a bed in this example, although it will be understood that it could be any other type of patient support apparatus) and make such data available to any other applications or servers running on the healthcare network 72. Local bed server is also configured to communicate and receive data from any other applications or servers (e.g. servers 90, not shown in FIG. 9) running on the healthcare network 72 and to forward such data to one or more patient support apparatuses 20 that are positioned within the healthcare facility. Such information includes, for example, patient information, patient room information, healthcare worker assignment information (e.g. which worker(s) are assigned to which patient(s)), and other information. Remote bed server 136 is capable of performing a variety of different functions, including gathering data from the sensors on board patient support apparatus 20a, and is accessible to patient support apparatus 20a through the Internet.

Software wireless access point 130 allows the patient support apparatus 20a to act as a local WiFi hotspot. Various devices having WiFi capabilities can connect to the access point 130 without having to undergo all of the healthcare facility's security, setup, and initialization procedures. Instead, such procedures, to the extent necessary, can be carried out locally at the patient support apparatus 20a. This enables the user of the wireless access point 130 to tether their device to wireless hotspot 130, enabling them to communicate with network 72 and/or the Internet 74. Further, the manufacturer of the patient support apparatus 20a can configure access point 130 to control the manner in which devices are granted access to access point 130.

Examples of some of the various types of devices that may communicate with a software WiFi access point 130 include, as shown in FIG. 9, a stretcher 120, a cot 122, one or pieces of furniture (such as a recliner) 124, and a handheld portable device 126 (which may be a smart phone, computer tablet, personal digital assistant, portable computer, or other device). Patient support apparatus 20a also includes a second transceiver 128, which in the embodiment shown in FIG. 9, is a Bluetooth transceiver that is in electrical communication with access point 130. Second transceiver 128 enables devices to access access point 130 using protocols different from the protocol of access point 130. As shown, a plurality of one or more patient personal devices 132 (e.g. smart phone, laptops, PDAs, etc.) may connect to WiFi access point 130 using their Bluetooth connection, instead of their WiFi connection. Alternatively, such devices can connect to access point 130 using a WiFi connection (if available).

Figure 10:
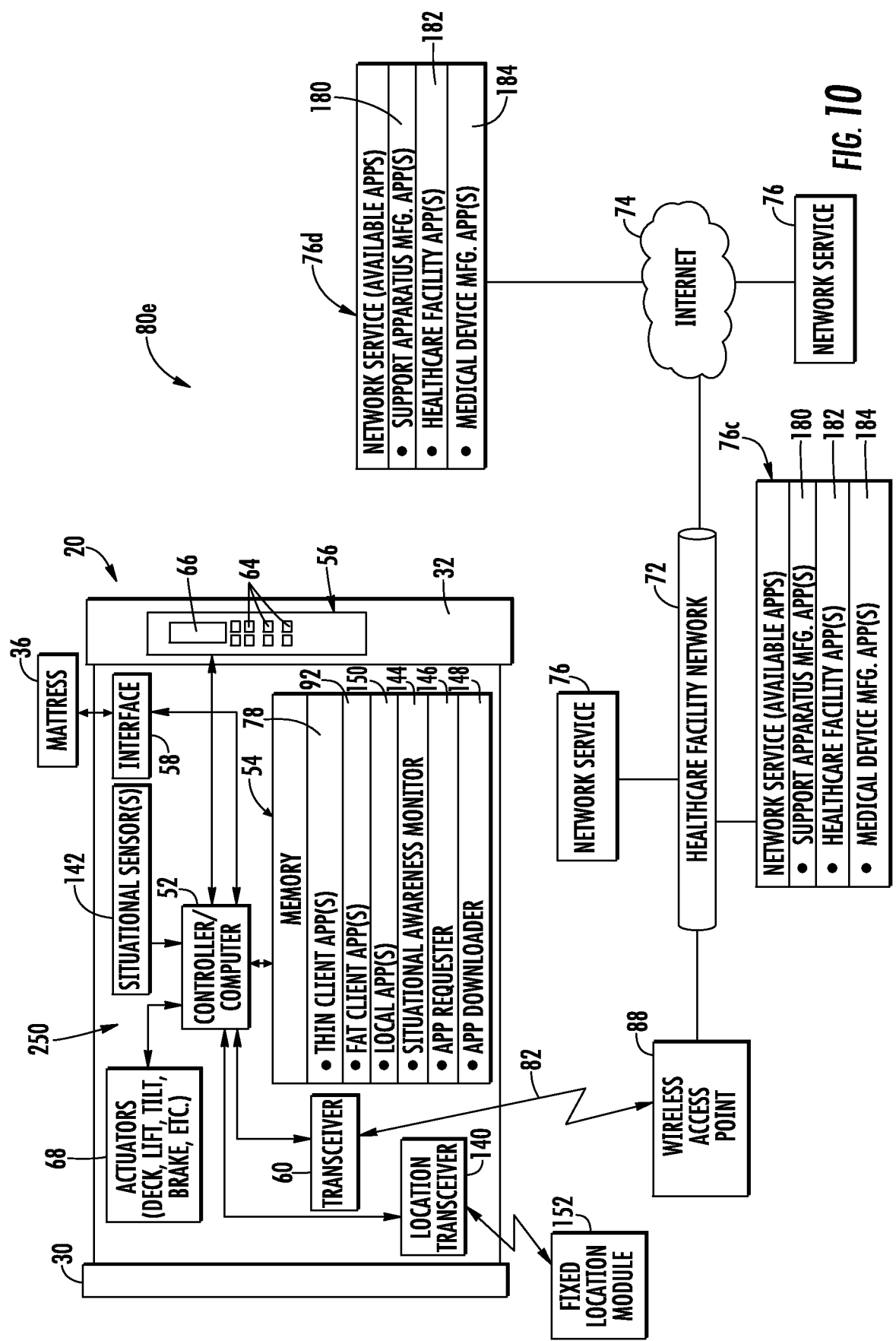
FIG. 10 is a diagram of another illustrative layout of a patient support apparatus having an first alternative control system shown in communication with a healthcare facility network.

FIG. 10 illustrates yet another example of a patient support apparatus software infrastructure layout 80e that can be implemented with one or more patient support apparatuses 20. As with layouts 80, 80a, 80b, 80c, and 80d, those components that are the same as those found in layouts 80, 80a, 80b, 80c, and/or 80d are labeled with the same reference number and operate in the same manner as has been previously described. Those components that are not found in layouts 80, 80a, 80b, 80c, and/or 80d are identified with a new reference number.

The patient support apparatus 20 of FIG. 10 includes a modified control system 250 that is different from the control system 50 of the previously described patient support apparatuses. Those components of modified control system 250 that are common to control system 50 are labeled with the same reference numbers, while those components that are new are identified with new reference numbers. More specifically, modified control system 250 and control system 50 both include the following components: a plurality of actuators 68, at least one transceiver 60, a controller 52, a memory 54, an interface 58, and a user interface 56 supported at a convenient location on the patient support apparatus for use by the caregiver, such as footboard 32. Modified control system 250 includes the following additional components: a location transceiver 140, one or more situational sensors 142, and a plurality of specific software applications, algorithms, and/or routines stored in memory 54. These software applications, algorithms, and/or routines include a situational awareness monitor 144, an application requester 146, and an application downloader 148. It will be understood by those skilled in the art that any one or more of these additional components can be incorporated into any of the patient support apparatuses described previously and depicted in FIGS. 1-10.

Memory 54 is also shown in FIG. 10 to include one or more local applications 150. Such local applications 150 are software applications that are purely local to patient support apparatus 20 and do not process any data remotely, unlike the thin or thick client applications discussed above. Although not shown in control system 50, memory 54 of control system 50 may also include one or more local applications 150 that are executed by controller 52.

Location transceiver 140 is adapted to communicate with one or more fixed location modules 152. Fixed location modules 152 are positioned in known locations throughout the healthcare facility and include unique identifiers that are correlated to their locations within the healthcare facility.

Location transceivers 140 are adapted to use near field communication, or other forms of communication, that have limited ranges so that transceiver 140 is only able to wirelessly communicate with fixed location module 152 when it is in close proximity thereto. Therefore, by determining the unique identifier associated with a specific location module 152 that a particular location transceiver 140 is able to communicate with, the correlation of that identifier to its location within the healthcare facility can be used to determine the location of the corresponding particular patient support apparatus 20 on which that particular transceiver 140 is located.

In one embodiment, location transceiver 140 is an infrared transceiver that is adapted to communicate with wall-mounted infrared location modules 152. Such location modules 152 are placed at pre-determined locations within a healthcare facility and can be used to distinguish between different bed-bays in non-private rooms that are adapted to house more than one patient (and, thus, more than one bed, or other type of patient support apparatus). In other embodiments, location transceivers 140 and location modules 152 may take on any of the forms and use any of the communication protocols disclosed in commonly-assigned U.S. Pat. No. 7,598,853 issued to Becker et al. and entitled LOCATION DETECTION SYSTEM FOR A PATIENT HANDLING DEVICE, the complete disclosure of which is incorporated herein by reference. Therefore, as but one example, location transceiver 140 may correspond to any of the receivers 54 disclosed in the '853 patent and fixed location module 152 may correspond to any of the locators 52 disclosed in the '853 patent. Location transceiver 140 and/or fixed location module 152 may also take on still other forms.

Situational sensor(s) 142 include one or more sensors supported on patient support apparatus 20 that are adapted to detect any one or more situations that are defined in memory 54 of patient support apparatus 20, as will be discussed in more detail below. In general, the detectable situations include any one or more of the following: the presence of a mattress 36 on top of patient support apparatus 20; the nearby presence of an individual (e.g. doctors, nurses, nurse's assistants, maintenance personnel, administrative personnel, cleaning personnel, visitors, etc.); the nearby presence of one or more medical devices (e.g. pumps, ventilators, monitors, hand-washing stations, biometric sensors worn by the patient, etc.); the presence of one or more nearby other patient support apparatuses 20, which may be of the same kind or different (e.g. a stretcher, bed, cot, recliner, operating table, or the like); and/or the location of patient support apparatus 20 within one or more specific locations within the healthcare facility (e.g. within a room containing oxygen supplies, or other flammable materials).

In one embodiment, patient support apparatus 20 includes a first set of situational sensors 142 that are adapted to detect a first set of situations, and a second set of different situational sensors 142 that are adapted to detect a second set of situations. For example, a first set of situational sensors 142 may include a plurality of near-field antennas that detect the presence of a nearby near-field transmitter (or transponder—which may be passive or active). The near-field transmitter is attached to any one or more of a mattress, a person, a medical device, another patient support apparatus, or a location module. The near-field transmitter is adapted to transmit a signal that identifies the type of object or person it is attached to (mattress, medical device, other support apparatus, location module, person and type of person, etc.). This signal is detected by the set of near field antennas that constitute the first set of situational sensors 142. Controller 52 processes these signals to determine what object or person is within a near-field transmission distance of the antennas 142. This nearby presence of these objects or persons are checked by controller 52 to see if they satisfy any of the pre-defined situations stored in memory 54. In this manner, situational sensors 142 are used to automatically determine the existence of one or more predefined situations.

As a second potential set of situational sensors 142, patient support apparatus 20 may include one or more situational sensors 142 that are adapted to detect line-of-sight electromagnetic signals, such as, but not limited to, infrared signals. Such signals are emitted by badges, tags, or other devices, that are either worn by personnel or attached to objects. The detection of these signals indicates that the badge, tag, or other device is within a nearby vicinity to the patient support apparatus, and that information is used by controller 52 to determine whether one or more predefined situations are have occurred.

In still other embodiments, situational sensors 142 may include sensors adapted to detect low power electromagnetic signals, such as radio frequency (RF) signals, that have a transmission range that is circumscribed to within a relatively short distance of the patient support apparatus 20 (due to their low power). The detection of these signals is interpreted by controller 52 as an indication that the device or person to whom the low power transmitter is coupled is positioned in nearby proximity to the patient support apparatus 20. If the close proximity of the device or person qualifies as meeting all of the conditions of the one or more predefined conditions stored in memory 54, then controller 52 determines that one or more situations are present. The consequences of such a determination are discussed in greater detail below.

In still other embodiments, the one or more situational sensors 142 can include one or more cameras (not shown). Such cameras may be positioned entirely off-board of patient support apparatus 20, entirely on-board patient support apparatus, or mixed between on-board and off-board locations. When positioned off-board patient support apparatus 20, the digital images recorded by the cameras may be pre-processed prior to forwarding them to controller 52, or they may be forwarded to controller 52 in their raw form for processing by controller 52. In either situation, controller 52 is adapted to analyze the contents of the images to determine whether they indicate the presence or absence of any one or more of the pre-defined situations stored in memory 54. In one embodiment, the situational sensors 142 include any one or more of the cameras disclosed in commonly-assigned U.S. patent application Ser. No. 13/242,022 filed Sep. 23, 2011 by applicants Richard Derenne et al. and entitled VIDEO MONITORING SYSTEM, the complete disclosure of which is hereby incorporated in its entirety herein by reference. The outputs of such cameras are either wholly, or partially, processed by controller 52 to determine the presence of one or more of the pre-defined situations.

In still other embodiments, the situational sensors 142 may include any one or more of the near field sensors disclosed in commonly-assigned U.S. patent application Ser. No. 13/802,992 filed Mar. 14, 2013 by applicants Michael Hayes et al. and entitled COMMUNICATION SYSTEMS FOR PATIENT SUPPORT APPARATUSES, the disclosure of which has already been incorporated herein by reference. Further, when any situational sensors 142 are incorporated into the patient support apparatus 20 that utilize the detection of near-field signals, the initial detection of such near-field signals may be subsequently followed by communication with the near-field device using far-field signals, in any of the manners disclosed in above-mentioned commonly-assigned U.S. patent application Ser. No. 13/802,992. Such subsequent far-field communication may include the transmission of not only data that identifies the specific individual or device to which the near field and far field transmitter is attached, but also additional information, such as, but not limited to, information from any sensors, processors, or other structures that are incorporated into the device containing the near field and far field transmitter.

The determination of whether or not any predefined situation is detected by situational sensors 142 is carried out by situational awareness monitor 144, which is stored in memory 54. Situational awareness monitor 144 includes one or more programs, routines, or algorithms run by controller 52 (or a portion of controller 52, such as an individual processor or microcontroller within controller 52) that take the outputs of situational sensors 142 and process them to determine if they represent the one or more conditions stored in memory 54 that define the one or more detectable situations. In other words, controller 52 uses situational awareness monitor 144 to continuously monitor whether or not patient support apparatus 20 is currently in any one or more of these predefined situations. In one embodiment, the predefined situations are statically coded into memory 54 during the manufacturing of patient support apparatus 20, while in other embodiments, the predefined situations are dynamically coded into memory 54 via communication with a network service 76 (using transceiver 60), and are thereafter able to be updated via communication with that network service 76.

Regardless of the source of the predefined situations, the predefined situations comprise a list of situations in which one or more specific software applications are applicable. That is, the predefined situations comprise a list of situations where patient support apparatus 20 will desirably carry out one or more additional software functions, using its existing hardware, than what it normally carries out during the absence of such situations, or what it was originally programmed to carry out after its initial sale. Thus, for example, the list of situations may include any one or more situations where any of the network services 76 discussed above would be useful. As noted, such network services include software applications that perform patient assessments, that monitor sensors, that monitor or schedule maintenance, that provide billing information, and/or that provide patient care protocol management. Therefore, situational awareness monitor 144 monitors when any situations arise where additional software would be useful and then, as will be explained below, automatically downloads that software to patient support apparatus 20 and executes the downloaded software. The downloaded software may be a thin client app, a thick client app, or a purely local app. Thus, situational awareness monitor 144 automatically monitors the situation of patient support apparatus 20 and automatically requests the use of one or more network services 76 (or other software apps) that are applicable to that specific situation. In this manner, a caregiver does not need to manually download any software for such services, but instead can rely upon this task being automatically performed by the patient support apparatus 20.

App requester 146 is the software used by controller 52 to request downloading software applications when situational awareness monitor 144 detects a situation for which a software application is relevant. Controller 52 uses app requester 146 to communicate with an "available apps" network service 76c that includes a copy of the software application that is to be automatically downloaded. As shown in FIG. 10, controller 52 uses app requester 146 to communicate a wireless request for the desired software application via communication with one or more wireless access points 88 of the healthcare facility network 72. The request may be to an "available apps" network service 76c that is local to the healthcare facility network 72, or it may be to an "available apps" network service 76d that is located on another network which is in communication with local network 72, such as a network connected to network 72 via the Internet 74. Regardless of the physical location of the "available apps" network service 76c or 76d, the "available apps" network service 76 is configured to transmit the appropriate software application that corresponds to the situation(s) identified by situational awareness monitor 144. The downloading of this corresponding software application is handled on the patient support apparatus 20 side by way of app downloader 148.

Once the appropriate software application is downloaded into memory 54 of patient support apparatus 20, controller 54—or an appropriate portion thereof—begins to automatically execute the downloaded software. As will be discussed in greater detail below, the executed software continues to run until an event happens that terminates its execution. After its execution terminates, controller 52 may automatically delete it from memory 54, or it may automatically retain a copy of it, or it may decide whether to delete or retain a copy of it based upon the current amount of free memory available on board patient support apparatus 20. In those instances where the software application is retained on-board patient support apparatus 20, the re-occurrence of the situation corresponding to that software (as detected by situational awareness monitor 144) will cause controller 52 to include in its request (sent via app requester 146) an indication that patient support apparatus 20 already includes a copy of the corresponding software. Such an indication will include an identity of the particular software application version currently on board patient support apparatus 20. The "available apps" network service (76c or 76d) will then compare this software version to the latest one it has available for forwarding to patient support apparatus 20. If the software version on board the patient support apparatus 20 is already the latest version, then the "available apps" network service 76c or 76d will not transmit a new copy of the corresponding software application, but will instead transmit a message indicating that the patient support apparatus 20 already has a copy of the latest corresponding software application, and it should use that copy instead of transmitting a new copy. Controller 52 will then begin executing a copy of that previously-downloaded copy of the software application. In this manner, needless downloading of already-downloaded software applications is avoided.

If the "available apps" network service 76c or 76d determines that the patient support apparatus 20 does not have the latest version of the corresponding software, it will begin downloading the latest version to patient support apparatus 20. In some instances, it may be possible to merely download updates to the previously-downloaded copy of the software application via the "available apps" network service 76c, 76d, thereby reducing the bandwidth usage by avoiding the re-transmission of software components that have not changed.

The ability of controller 52, via situational awareness monitor 144, app requester 146, and app downloader 148, to automatically obtain copies of software applications that are useful and relevant to particular situations in which the patient support apparatus 20 is in improves the overall functionality of the patient support apparatus, and automatically ensures that the latest software versions and capabilities are incorporated into the patient support apparatus 20.

Figure 11:
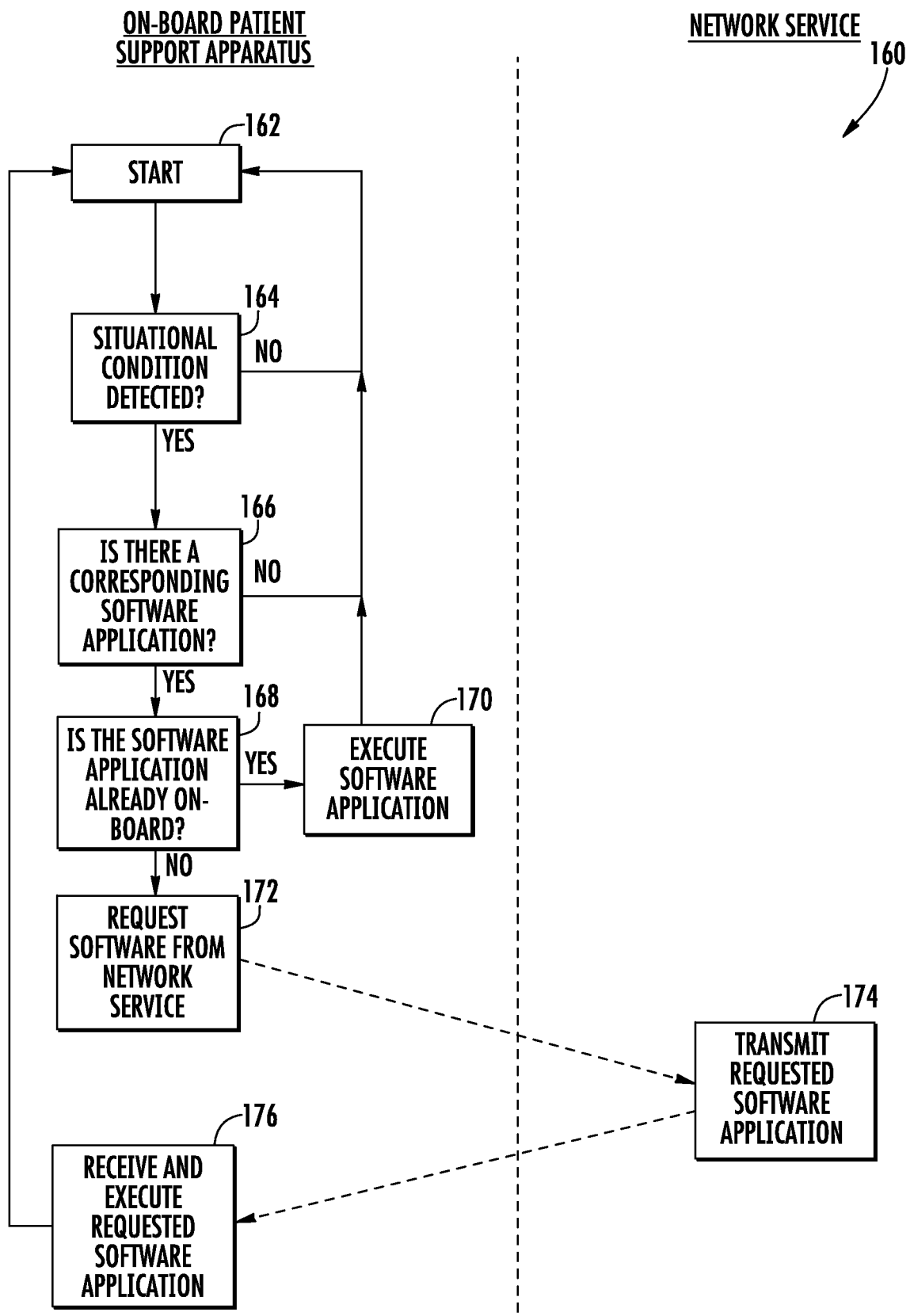
FIG. 11 is a flowchart of an illustrative automatic application retrieving algorithm that may be used with the first alternative control system of the patient support apparatus of FIG. 10.

Before turning to FIG. 11 and its detailed flowchart of the algorithm used for automatically obtaining relevant software applications, it may be useful to provide a few examples of the types of software applications that are downloadable by patient support apparatus 20 using app requester 146 and app downloader 148. One example of a software application that can be automatically downloaded by patient support apparatus 20 is software used to control and/or communicate with a mattress 36 positioned on top of the patient support apparatus 20. In this example, the situation detected by one or more situational sensors 142 is the presence of a mattress 36 positioned on support surface 28 of patient support apparatus 20. Such situational sensors may be near field sensors that communicate with a near field transmitter on the mattress 36, or they may be any of the other types of situational sensors described above.

In addition to merely detecting the presence of mattress 36, patient support apparatus 20 is also adapted to detect the type of mattress 36 positioned on patient support surface 28. This type of detection may include a specific serial number, or product number, or it may include a more general model of mattress 36. By including this information, situational awareness monitor 144 is able to determine whether there are any software applications that correspond to this specific serial number, product number, or model of mattress 36. Patient support apparatus 20 is therefore automatically able to download the appropriate software application used to control and/or communicate with the specific type of mattress 36 positioned thereon. If the mattress 36 is later changed to a different model or type that has different functionalities, or a different communication interface, situational awareness monitor 144 is configured to automatically detect this new type of mattress 36 and obtain, via network service 76c or 76d, the corresponding software application that pertains to that specific type of mattress.

By designing patient support apparatus 20 so that it is not statically constrained to work with only one type of mattress, or a limited number of mattresses, but instead is able to dynamically obtain any corresponding mattress software applications, patient support apparatus 20 allows hospitals to not only use a variety of different mattresses 36 with a given patient support apparatus 20 without losing any functionality, but also allows the software used to control the patient support apparatus 20 to be automatically updated so as to enable the hospitals to capture the latest improvements, features, and modifications to the mattresses 36 and the control and/or communication with the mattresses 36.

The mattress software application(s) that are downloaded via app downloader 148, in conjunction with "available app" network service 76c or 76d, utilize the existing hardware present on patient support apparatus 20, as well as the hardware contained with the mattress 36 to carry out this control/communication. Thus, for example, the downloaded software application will interact with the mattress 36 via interface 58. Further, the downloaded software application will likely also communicate with user interface 56 on the footboard 32 of patient support apparatus 20. Such communication may include the displaying of one or more icons, controls, or other information on display 66 of user interface 56, as well as the monitoring of, and reaction to, the pressing of one or more buttons 64. The downloaded software application, in some embodiments, will take over the control of all or a portion of screen space on display 66, at least for certain amounts of time. The software application may also display on display 66 any or all of the features that can be controlled on the mattress 36, as well as the means for exercising control over those features. Such features may include inflating the mattress, deflating the mattress, redistributing patient interface pressure over the mattress, setting levels of patient immersion into the mattress, performing therapy on the patient using the mattress (such as percussion therapy), assisting in patient turning by inflating one or more side bladders, and performing still other functions. By utilizing the existing user interface 56 on patient support apparatus 20, it is not necessary for the mattress 36 to include its own user interface, but instead can rely upon the user interface already incorporated into patient support apparatus 20.

In addition to utilizing the interfaces and user interfaces on-board the patient support apparatus 20, the downloaded mattress software application may also utilize the existing alarm hardware and/or communications hardware on board the patient support apparatus 20. For example, some mattresses 36 may include built-in sensors that detect when a patient has, or is about to, exit from the patient support apparatus. Such sensors may include air pressure sensors, pressure sensors, or other conventional sensors. When so equipped, this information is passed to controller 52 via interface 58 (under the control of the mattress software application) so that controller 52 can issue an alarm when the patient has exited, or is about to exit. In other words, controller 52—under the control of the downloaded software application—uses the existing audio or visual hardware on board patient support apparatus 20 to provide an alarm indication when the patient has exited, or is about to exit, from the patient support apparatus 20, as detected by sensors incorporated into mattress 36. Such hardware may include one or more beepers, speakers, lights, or the like. Still further, controller 52 may send a signal to a nurse call system coupled to the patient support apparatus, and/or it may send a signal via transceiver 60 to one or more servers in communication with the healthcare facility network 72.

When mattress 36 is so equipped with patient exit detection sensors, this allows a patient support apparatus 20 that does not have patient exit detection capability by itself to be easily converted to a patient support with such exit detection capability through the simple addition of an appropriate mattress. Further, as advances and/or changes are made to the exit detection algorithms and/or sensors of specific mattresses 36, these can be automatically incorporated into the patient support apparatus 20 through situational awareness monitor 144 and its associated automatic downloading of the corresponding control software application.

One illustrative type of mattress 36 that may be used with patient support apparatus 20 and controlled, either partially or wholly, via software running on controller 52, includes any of the mattress embodiments disclosed in commonly assigned U.S. patent application Ser. No. 13/836,813 filed Mar. 15, 2013 by applicants Patrick Lafleche et al. and entitled INFLATABLE MATTRESS AND CONTROL METHODS, or U.S. patent application Ser. No. 61/697,010 filed Sep. 5, 2012 by applicant Patrick Lafleche and entitled PATIENT SUPPORT, the complete disclosures of both of which are hereby incorporated herein in their entirety by reference. It will be understood by those skilled in the art, however, that other types of mattresses may be used with patient support apparatus 20.

Another type of software application that is downloadable by patient support apparatus 20 using app requester 146 and app downloader 148 is one that controls one or more aspects of patient support apparatus 20 based upon its current location with a healthcare facility. As one example, if one or more of situational sensors 142 detect that patient support apparatus 20 is currently located in a healthcare facility room that contains, or is likely to contain, the flammable materials (the location of patient support apparatus 20 in this location may also, or alternatively, be detected by transceiver 140 and fixed location modules 152), then situational awareness monitor 144 will utilize app requester 146 and app downloader 148 to download a software application that changes how patient support apparatus 20 is controlled. Specifically, due to the likely presence of flammable materials, such as oxygen, the control of patient support apparatus 20 can be modified by a downloaded software application that prevents activation of any of the motors on board patient support apparatus 20. By disabling the activation of the motors while patient support apparatus 20 is in the presence of flammable materials, the possibility of a spark created by the activation of the motors is eliminated. Accordingly, the control of patient support apparatus 20 can be automatically modified to adjust to its surroundings.

Such a downloaded software application will not only disable the motors and/or take other steps likely to prevent the possibility of a fire, it will also display the fact of this motor disablement on the display 66 so that caregivers are made aware of this automatic disablement of the motors. Further, an aural or visual indication may be provided so that the patient is also aware of the disablement of the motors. Such aural or visual indications to both the patient and caregivers help prevent mistaken conclusions that patient support apparatus 20 is defective.

Another type of software application that is downloadable by patient support apparatus 20 using app requester 146 and app downloader 148 is one that enables patient support apparatus 20 to communicate with a second patient support apparatus that is positioned within the vicinity of patient support apparatus 20. Such communication may include any desirably communication, including not only patient information (name, identification, medical data, etc.), but any useful information about one or more patient care protocols that have been set up for taking care of that particular patient. For example, in many settings, it is customary for a patient who enters a hospital through the emergency room to first be placed on a stretcher. From the stretcher, the patient may thereafter be transferred to a stretcher. After the stretcher the patient may be transferred to a bed. Once on the bed, the patient may again be transferred back to a stretcher for transport to different locations within the hospital. In many instances, it is desirable to know what patient support apparatus (cot, stretcher, or bed) that patient is currently associated with. Further, it is also desirable in many situations for information about the patient to be transferred from one patient support apparatus to the other as the patient moves between these different patient support apparatuses. Accordingly, one type of software application that can be downloaded is a software application that allows the patient support apparatus 20 to communicate wirelessly with another nearby patient support apparatus so that any information associated with that patient is passed with the patient as he or she is moved to the other nearby patient support apparatus.

As with the mattress software applications, situational sensors 142 not only detect the presence of a nearby second patient support apparatus, they also detect they type of patient support apparatus. Such type information may include not only information indicative of whether the patient support apparatus is a cot, stretcher, bed, recliner, operating table, or the like, but also manufacturer information and/or specific model information. This information is included in the message sent out by app requester 146 to the "available apps" network service 76c, 76d so that the network service 76c, 76d can locate the necessary software application that enables communication with that specific type of patient support apparatus. Once this software application is downloaded, controller 52 executes it so that it is able to communicate with the second nearby patient support apparatus and receive and/or transmit patient information to or from the second nearby patient support apparatus. This avoids the task of the caregiver manually transferring this information from one patient support apparatus 20 to the next. Further, by having this software application downloadable from the network service 76c, 76d, the patient support apparatus 20 can be automatically configured to communicate with new patient support apparatuses that may use different communication protocols, or that are capable of conveying different types of data than other types of patient support apparatuses.

Still another type of software application that is downloadable by patient support apparatus 20 using app requester 146 and app downloader 148 is one that enables patient support apparatus 20 to communicate with a nearby medical device. The medical device may be any of a variety of different types of medical devices that are positioned within the vicinity of patient support apparatus 20, such as, but not limited to, pumps, ventilators, monitors, vital signs sensors, etc. Situational sensors 142 not only detect the presence of the nearby medical device, they also detect they type of medical device. Such type information may include not only information indicative of whether the medical device is a pump, monitor, ventilator, vital sign sensor, etc., but also the manufacturer and/or specific model of the medical device. This information is included in the message sent out by app requester 146 to the "available apps" network service 76c, 76d so that the network service 76c, 76d can locate the necessary software application that enables communication with that specific type of medical device. Once this software application is downloaded, controller 52 executes it so that it is able to communicate with the medical device and receive and/or transmit patient information to or from it. By having this software application downloadable from the network service 76c, 76d, the patient support apparatus 20 can be automatically configured to communicate with new medical devices that may use different communication protocols, or that are capable of conveying different types of data than other types of medical devices.

The types of medical devices to which patient support apparatus 20 may communicate are myriad. In some instances, such devices may not include their own user interface, but instead rely upon all or a portion of user interface 56 of patient support apparatus 20 to communicate information to a human, or to receive instructions from a human. Alternatively, some of such devices can use the display 66 and/or user interface 56 of the patient support apparatus 20 as a supplemental display or user interface that supplements an already existing user interface on the medical device. As was noted previously, in some instances, the medical device may be a patient interface pressure sensing mat, such as, but not limited to, the flexible pressure sensing mats disclosed in commonly assigned PCT patent application serial number PCT/US12/27402, filed Mar. 2, 2012 by Stryker Corporation, and entitled SENSING SYSTEM FOR PATIENT SUPPORTS, the complete disclosure of which has already been incorporated herein by reference. The information derived from the pressure sensing may be displayed on display 66, and buttons 64 may be used to control one or more aspects of the pressure sensing mats.

Another type of software application that is downloadable by patient support apparatus 20 using app requester 146 and app downloader 148 is one that is used for billing purposes. Such a software application may monitor the length of time that a patient uses patient support apparatus 20, or the length of time that any of the person's or devices mentioned above are in physical proximity to patient support apparatus 20 (i.e. the amount of time that any of the aforementioned situations or conditions are present). By keeping track of the amounts of time that such devices are used, or are otherwise associated with a particular patient, a healthcare facility can use that information to generate invoices that are more reflective of the actual amount of medical resources used by a particular patient. Such software applications may be updated periodically through network services 76c or 76d to reflect new billing criteria. Further, such software applications may be configured to automatically transmit their accumulated usage information to a remote server that uses such information to generate invoices.

FIG. 11 illustrates one example of a situation-dependent software retrieval algorithm 160 that is partially carried out by modified control system 250 of patient support apparatus 20 and partially carried out by network service 76c or 76d. Algorithm 160 begins at an initial start step 162 which is immediately followed by an evaluation step 164. Evaluation step 164 is carried out by controller 52 using the data gained from situational sensors 142 and comparing the gathered data to the criteria stored in memory 54 that defines the one or more situational conditions (e.g. the presence of a nearby person or device, or the location of patient support apparatus 20 in a specific location). If none of the data gathered from sensors 142 meets the criteria of one or more situations, as determined in step 164, controller 52 returns to start step 162 and the algorithm 160 repeats itself. If, however, controller 52 determines at step 164 that one or more situational conditions are present, controller 52 proceeds to step 166 where it determines if there are any software applications that correspond to one or more detected situational conditions. If there are none, controller 52 returns to start step 162.

If controller 52 determines at step 166 that at least one software application corresponds to the detected situation(s), controller 52 proceeds to step 168 where it determines whether the corresponding software application is already stored on board patient support apparatus 20. Controller 52 performs this step by examining the contents of memory 54 or the contents of any other memories on board patient support apparatus 20 where such a software application might be stored. If controller 52 determines at step 168 that the corresponding software is already aboard patient support apparatus 20, it proceeds to step 170 where it begins to execute the on-board software.

If controller 52 determines at step 168 that the corresponding software application is not on-board, it proceeds to step 172 where it requests a copy of the corresponding software from network service 76c and/or 76d. Request step 172 is carried out by sending one or more appropriate messages to healthcare facility network via transceiver 60 which, as noted above, is a WiFi transceiver in some embodiments, or any other suitable transceiver can be used. The request sent at step 172 is conveyed by healthcare network 72 to network service 76c or 76d, which, at step 174 processes the request and begins transferring the requested software application. The particular software application that is transmitted by network service 76c or 76d is either stored in memory local to network 76c, d, or it is stored remotely and service 76c or d is configured to retrieve it from this remote location and transmit it to the requesting patient support apparatus 20. At step 176, controller 52 receives the transmitted software application and begins executing it, while thereafter returning to start step 162.

In an alternative embodiment, as part of step 168, controller 52 not only checks to see if the corresponding software application is on-board or not, but also checks the software application version. This version is then forwarded to network service 76c or 76d, which checks to see if the reported version is the latest version or not. If it is, the service 76c or 76d communicates that information back to controller 52 and controller 52 proceeds to step 170, where it begins executing the on-board software. If, however, the service 76c or 76d determines that the software version is not the latest software version, it will transmit the latest version of the software application at step 174, which will be received and executed at step 176 in the manner described above. In some embodiments, the transmission of the latest software version will reduce bandwidth usage by transmitting only those components of the software application that have changed from the version already on-board patient support apparatus 20, while in other embodiments, the latest version of the entire software application will be transmitted.

It will be understood that the downloaded and executed software application may, during its execution, utilize one or more different network services 76, 76a, etc. That is, simply because the software application was transmitted from one of network services 76c or 76d, this does not mean that the execution of the software application on patient support apparatus 20 requires further interaction with network services 76c or 76d, nor does it preclude the network service from interacting with other network services 76. As one example, a thin client software application 78 downloaded from network service 76c may, after being downloaded and executed by controller 52, proceed to interact with network service 76. In still another embodiment, the downloaded software application may be an entirely local application that, once downloaded, does not subsequently interact with any network services 76.

FIG. 10 shows a classification of the software applications that are available from network services 76c or 76d based upon the authors or providers of the software applications. For example, FIG. 10 shows the software applications that are available from network services 76c or 76d divided between support apparatus manufacturer apps 180 (i.e. those provided by the manufacturer of the patient support apparatus 20), healthcare facility apps 182 (i.e. those provided by the proprietors of the healthcare facility in which the patient support apparatus 20 is located), and medical device manufacturer apps 184 (i.e. those provided by the manufacturers of medical devices). Of course, additional categories of software applications may also be stored, or otherwise made accessible, at network services 76c and/or 76d. Such additional categories include, but are not limited to, software applications that are the result of collaboration between two or more types of the software apps just mentioned (i.e. apps 180, 182, and 184).

As was noted previously, one type of support apparatus manufacturer app 180 is a software application that controls the communication between the patient support apparatus 20 and the mattress 36 positioned thereon. Another type of support apparatus manufacturer app 180 is a software application that allows patient support apparatus 20 to communicate data directly with one or more other patient support apparatuses 20. An example of a healthcare facility app 182 is a software application that is used by caregivers to perform patient assessments (e.g. fall risk, bed sore risk, etc.) and/or to implement, monitor, or create patient care protocols. An example of a medical device manufacturer app 184 is a software application that allows the patient support apparatus 20 to communicate with a medical device positioned in the vicinity of the patient support apparatus 20, such as a pump, ventilator, vital signs sensor, temp sensor, or other patient sensor. Still other types of software applications are, of course, possible.

From FIG. 10 and the foregoing description, it can be seen that network services 76c and 76d are comparable to conventional app "stores" that allow user of mobile devices (e.g. cell phones, tablets, etc.) to download software applications to their mobile device. Network services 76c and 76d, however, differ from conventional app "stores" in that they download software applications to patient support apparatuses 20. They also differ in that such downloads need not be performed manually by a user actively connecting to services 76c or 76d, browsing for available apps, and then manually implementing the download process. Instead, such "browsing" and downloading are performed automatically. Further, in some of the embodiments described above, not only does the patient support apparatus automatically download available apps from network service 76c or 76d, but the patient support apparatus 20 is smart enough to know when to perform such automatic downloading. That is, as has been described, the patient support apparatus 20 continually monitors its current situation and, when it detects any one or more predefined situations, begins the process of automatically downloading software applications from services 76c or 76d, if such applications are not already on board the patient support apparatus 20, or if the latest version of those applications are not already on board the patient support apparatus 20. Caregivers, technicians, and maintenance personnel are therefore are relieved from the task of having to manually update, install, or configure the patient support apparatuses 20. Instead, patient support apparatuses 20 are automatically provided with the latest software applications, as well as being automatically provided with software applications that are particular to the specific situations the patient support apparatus 20 is subjected to.

Figure 12:
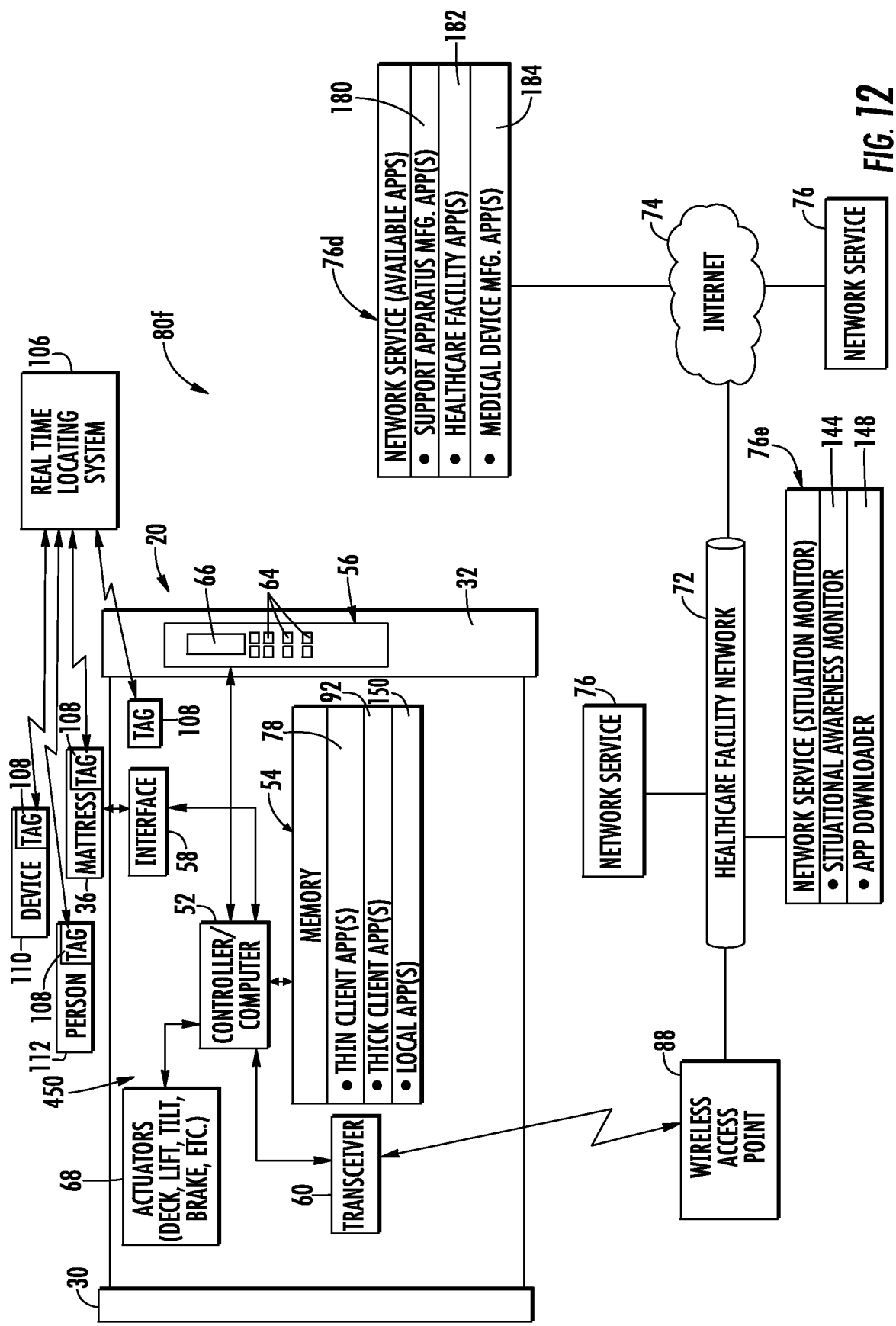
FIG. 12 is a diagram of another illustrative layout of a patient support apparatus having a second alternative control system shown in communication with a healthcare facility network.

FIG. 12 illustrates yet another example of a patient support apparatus software infrastructure layout 80f that can be implemented with one or more patient support apparatuses 20. As with layouts 80-80e, those components that are the same as those found in layouts 80-80e are labeled with the same reference number and operate in the same manner as has been previously described. Those components that are not found in layouts 80-80e are identified with a new reference number.

Layout 80f differs from layout 80e primarily in that the computational task of determining whether one or more predefined situations is present has been offloaded from the patient support apparatus 20 to a remote location. That is, patient support apparatus 20 of FIG. 12 does not need to include any situational sensors 142, nor does it need to include a location transceiver 140. Instead, the location of both patient support apparatus 20 and any people or objects within its vicinity is determined by a real time locating system 106 that is in communication with a plurality of RF ID tags 108, or other types of tags 108. Real time location system 106 reports the location of all of the tags 108 that it detects to a network service 76e that monitors these locations and processes them to determine if one or more predefined situations are present. That is, network service 76e includes situational awareness monitor 144 and app downloader 148. These software modules 144 and 148 were located onboard the patient support apparatus 20 in layout 80e of FIG. 10, but have been moved to the network in the layout of FIG. 12.

Situational awareness monitor 144 analyzes the location information provided from real time locating system 106 and compares it to the criteria stored in its memory (or otherwise accessible to monitor 144) that define the one or more situations where there is a corresponding software application. Typically, these situations will be situations where a specific type of object is located within a specified distance to another object. One common situational definition will be a situation where one of the tags 108 is located within a specified proximity to patient support apparatus 20. The tag in proximity to patient support apparatus 20 may be attached to a medical device 110, or to a person 112, or to mattress 36, or to other objects.

For example, if situational awareness monitor 144 determines that a tag 108 attached to a mattress 36 is in close proximity to the patient support apparatus 20 (as determined by system 106's monitoring of the tag 108 attached to support apparatus 20), monitor 144 will conclude that the mattress 36 is positioned on top of support apparatus 20 and search for any software applications that can be used by patient support apparatus 20 to control one or more aspects of mattress 36, or to otherwise communicate information between patient support apparatus 20 and mattress 36. As another example, different personnel in a healthcare facility may wear tags or badges 108 that either identify that person individually, or identify the class of worker to which that individual belongs (e.g. doctor, nurse, nurse's assistant, records administrator, clergy, maintenance personnel, janitor, etc.). When situational awareness monitor 144 detects that a specific individual, or an individual who is assigned to a specific class of workers, is within a defined proximity to patient support apparatus 20, situational awareness monitor 144 will look to see if there is any corresponding software applications that correspond to that particular situation. For example, the approach of maintenance personnel may result in a diagnostic and/or maintenance software application being automatically downloaded to the patient support apparatus 20.

Once situational awareness monitor 144 determines that a situation is present that corresponds to a software application, the corresponding software application is downloaded to the specific patient support apparatus 20 via app downloader 148, in the same manner as has been previously described. In layout 80f of FIG. 12, the downloading takes place by retrieving the corresponding software application from network service 76d, which is not local to the network 72, but instead is accessible over the Internet. That is, once monitor 144 determines that a software application corresponds to the detected situation, it contacts network service 76d and has the corresponding software application downloaded to patient support apparatus 20, under the coordination of app downloader 148. Such downloading may occur via direct transmission of the software application from network service 76d to the patient support apparatus 20, or it may occur by first transmitting the software application to network service 76e, which then forwards the software application to the patient support apparatus 20.

It will be understood by those skilled in the art, of course, that network service 76e can be modified from the configuration shown in FIG. 12 to include one or more software applications that are stored therein such that it does not need to retrieve the software applications from service 76d. That is, in some embodiments, network service 76e may be modified from the configuration shown in FIG. 12 by combining network service 76d together with network service 76e. When so combined, the combined service may be located either locally on network 72, or at a remote location accessible via the Internet, or by other means.

It will also be understood by those skilled in the art that, although FIGS. 10 and 12 only depict a single patient support apparatus 20, multiple patient support apparatus 20 will typically be in communication with the various network services 76. That is, multiple patient support apparatus 20 within a given healthcare facility will typically be in communication with a common network service, such as any one or more of services 76a, 76b, 76c, 76d, and/or 76e. All such patient support apparatuses 20 within the healthcare facility will therefore automatically be provided with the software applications that correspond to the detected situations.

Real time locating system 106 may be any conventional real time locating system that is commercially available, or it may be any unconventional real time locating system that otherwise provides the function of determining the location of any tagged assets within an environment. Conventional real time locating system customarily use RF ID tags, which may be used in the layout 80f of FIG. 12, although other types of tags 108 may also be used. Real time locating system 106, in addition to reporting location information to network service 76e, may also report location information to one or more other services or servers that are located on network 72, or on other networks.

Figure 13:
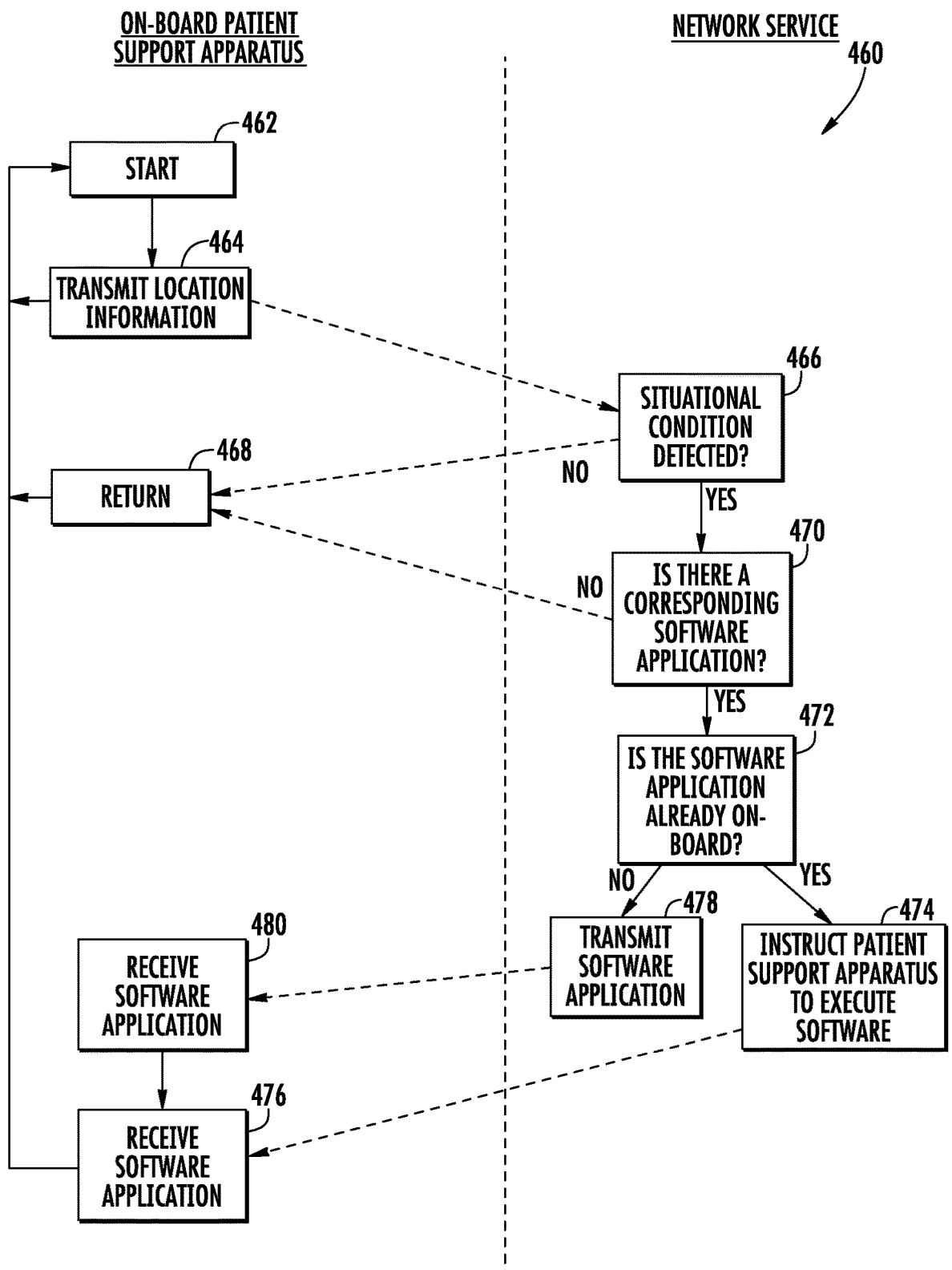
FIG. 13 is a flowchart of an illustrative automatic application retrieving algorithm that may be used with the second alternative control system of the patient support apparatus of FIG. 12.

FIG. 13 illustrates another example of a situation-dependent software retrieval algorithm 460 that is partially carried out by control system 450 of patient support apparatus 20 and partially carried out by network services 76e and 76d (whether they are separate or combined). Algorithm 460 begins at an initial start step 462 which is immediately followed by a location transmission step 464. Location transmission step 464, in the embodiment shown in FIG. 12, is carried out by the tag 108 that is coupled to patient support apparatus 20. That is, tag 108 transmits a signal to system 106 that is detected by system 106 and used to determine the location of tag 108. The transmission of this signal may be actively powered by a power source on board patient support apparatus 20, or it may be passive, in which case the energy of this signal is provided by an initial interrogation signal broadcast by system 106 and detected by tag 108.

After system 106 determines the location of patient support apparatus 20, it forwards that information to network service 76e, which determines at step 466 whether or not a predefined situation exists or not. Step 466 is carried out by comparing the location of patient support apparatus 20 to the location of any and all other devices or persons that have a tag 108 attached thereto. In other words, in addition to receiving the location of patient support apparatus 20 from system 106, network service 76e also receives the location of the tags 108 which are attached to other devices and/or personnel. When those devices or personnel are within a defined distance of patient support apparatus 20, or each other, service 76e determines that a predefined situation exists. If no such situations are determined to currently exist, control passes back to a return step 468, which in turn causes the repetition of location transmission step 464.

If situational awareness monitor 144 of network service 76e determines at step 466 that a condition has been detected, it proceeds to step 470 where it determines whether a corresponding software application is available from for the identified situation. If the available software is defined by another network service, such as service 76d, situational awareness monitor 144 will contact the service 76d during step 470. If services 76d and 76e are combined together, then monitor 144 need not communicate with any outside entities during the performance of step 470. If no corresponding software is available, control passes back to return step 468.

At step 472, situational awareness monitor 144 determines whether the corresponding software is already on board patient support apparatus 20 or not. This is accomplished either by consulting a table maintained by monitor 144 that keeps track of all of the software currently on-board each patient support apparatus 20 (as well as the version number of the software), or by sending an interrogation message to patient support apparatus 20 via transceiver 60 and waiting for a response. If the corresponding software is already on-board the patient support apparatus 20, then control passes to step 474 where service 76e instructs the patient support apparatus 20 to begin executing the corresponding software. This is accomplished by sending a message to controller 52 on-board patient support apparatus 20 via transceiver 60, which responds to the receipt of such a message at step 476 by executing the corresponding software application. If the corresponding software is not already on-board the patient support apparatus 20, the app downloader 148 proceeds to transmit the corresponding software application to patient support apparatus 20 via transceiver 60 at step 478. Controller 52 on-board patient support apparatus 20 receives the transmitted software application at step 480 and begins executing it at step 476 after the application has been received.

It will be understood by those skilled in the art that algorithm 460 illustrated in FIG. 13 may be modified in a variety of different ways. As one example, algorithm 460 may be modified to accommodate a patient support apparatus 20 that includes location transceiver 140, but does not include any situational sensors 142 or a tag 108. Such a patient support apparatus 20 will be able to detect its own location (via fixed location modules 152), but will rely upon a real time locating system 106 that detects tags 108 on medical devices 110, people 112, and/or mattresses 36 to determine the location of these other entities. In order to determine whether one or more predefined situations are present, the location of the patient support apparatus 20 and the other entities will be compared with each other, either on-board patient support apparatus 20 or at a remote location. Algorithm 460 can thus be modified to accommodate this hybrid-location system where the patient support apparatus 20 uses a separate system (transceiver 140 and modules 152) to determine is location than the real time locating system 106 used to determine the location of the other entities. Still other modifications of algorithm 460 are possible.

It will be understood that the predefined situations that cause software applications to be automatically transmitted to a patient support apparatus 20 (if they are not already on-board) may be defined by different entities. As one example, the owner or operator or the healthcare facility may define the situations through a user interface that allows the owner or operator to configure the network service 76c and/or 76e. Alternatively, or additionally, network service 76e may be in periodic communication with another network service available over the Internet that defines the situations. Such an Internet service could be maintained by the manufacturer of the patient support apparatus 20, or by an entity authorized by the manufacturer of the patient support apparatus 20. As yet another alternative, the manufacturer(s) of one or more medical devices 110 or mattresses 36 may maintain, or provide updates to, a network service that acts as a repository of the predefined situations (e.g. network service 76*e*) or that communicates with situational awareness monitor 144.

The available apps network service 76*c* or 76*d* may be configured such that the service will only download certain corresponding apps if the healthcare facility that owns the patient support apparatus 20 has paid one or more fees. In other words, the software applications that are available for a particular patient support apparatus 20 may vary depending upon fees paid by the healthcare facility that owns the patient support apparatus 20. The fees may be arranged in tiered structures that enable the downloading of some applications for free, others for a first fee, and still others for a second fee.

When patient support apparatus 20 is implemented as a recliner, it may be a recliner such as that disclosed in commonly assigned U.S. patent application Ser. No. 61/791, 255 filed Mar. 15, 2013 by applicant Richard Derenne and entitled MEDICAL SUPPORT APPARATUS, the complete disclosure of which is incorporated herein by reference. Other types of recliners may, of course, be used.

Various alterations and changes can be made to the above-described embodiments without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

What is claimed is:

1. A patient support apparatus comprising:
a frame;
a patient support surface supported on the frame;
a transceiver adapted to communicate with a remote network;
a display; and
a computer supported on the patient support apparatus and in communication with the display, the computer adapted to control at least one function of the patient support apparatus, and the computer including a software platform for supporting a plurality of software-as-a-service (SaaS) applications, a first one of the SaaS applications provided by a first network service available on the remote network and a second one of the SaaS applications provided by a second network service on the remote network, the first SaaS application providing data for at least one of the following functions: (a) assisting a caregiver to assess a bed sore risk of a patient; (b) assisting a caregiver to assess a fall risk of a patient; and (c) and determining when a patient may be about to exit the patient support apparatus; and whereby the computer is further adapted to allow a user to choose whether the computer executes the first SaaS application, the second SaaS application, both the first and second SaaS applications, or neither of the first and second SaaS applications.

2. The patient support apparatus of claim 1 further including a plurality of force sensors adapted to detect information about a position of a patient on the support surface, the first SaaS application adapted to forward information generated from the force sensors to the first network service and receive processed information back from the first network service.

3. The patient support apparatus of claim 2 wherein the processed information includes information indicating at least one of the following: (1) that a patient has or has not turned while positioned on the patient support apparatus; (2) that the patient may be about to exit from the support surface; and (3) whether the patient on the support surface is asleep or not.

4. The patient support apparatus of claim 1 wherein the second SaaS application generates billing information based on usage of the patient support apparatus.

5. The patient support apparatus of claim 1 wherein the first SaaS application determines when a patient may be about to exit the patient support apparatus and the second SaaS application indicates how often a patient supported on the patient support apparatus should be turned.

6. The patient support apparatus of claim 1 wherein the first and second SaaS applications control at least a portion of screen space on the display.

7. The patient support apparatus of claim 3 wherein the patient support apparatus is one of a bed, a stretcher, a cot, a recliner, and an operating table.

8. The patient support apparatus of claim 7 further including:
an elevation adjustment mechanism adapted to raise and lower the frame;
at least one motor adapted to pivot a section of the support surface about a generally horizontal axis;
a plurality of siderails coupled to the frame; and
a control panel having controls for controlling the elevation adjustment mechanism and the motor.

9. The patient support apparatus of claim 1 wherein the first SaaS application provides data for performing at least one of functions (a) and (b) and provides a list of questions for assessing an aspect of a patient supported on the patient support apparatus, the list of questions is controllable by an employee of a healthcare facility in which the patient support apparatus is positioned, and the first SaaS application displays the list of questions on the display.

10. The patient support apparatus of claim 9 wherein the list of questions provides an assessment of at least one of the following: a patient's susceptibility to developing bed sores and a patient's fall risk.

11. A patient support apparatus comprising:
a frame;
a patient support surface supported on the frame;
a transceiver adapted to communicate with a remote network;
a display; and
a computer supported on the patient support apparatus and in communication with the display, the computer adapted to control at least one function of the patient support apparatus, and the computer including a software platform for supporting a plurality of software-as-a-service (SaaS) applications, a first one of the SaaS applications provided by a first network service available on the remote network and a second one of the SaaS applications provided by a second network service on the remote network, the first one of the SaaS applications adapted to execute a patient care protocol, wherein the first network service is configurable by employees of a healthcare facility in which the patient support apparatus is positioned such that the employees are able to customize what information the first SaaS application uses when executing the patient care protocol; and whereby the computer is further adapted to allow a user to choose whether the computer executes the first SaaS application, the second SaaS application, both the first and second SaaS applications, or neither of the first and second SaaS applications.

12. The patient support apparatus of claim 11 further comprising:

first and second actuators, the first actuator adapted to move a first component on the patient support apparatus, and the second actuator adapted to move a second component on the patient support apparatus different from the first component;

wherein the second SaaS application is a maintenance software application adapted to perform the following: (a) total a first number of times the first actuator is actuated and total a second number of times the second actuator is actuated, (b) compare the first number to a first threshold, (c) compare the second number to a second threshold, and (d) issue a maintenance alert if either the first number exceeds the first threshold or the second number exceeds the second threshold.

13. The patient support apparatus of claim 12 wherein the computer is further adapted to forward the maintenance alert to the second network service available on the remote network.

14. The patient support apparatus of claim 13 wherein the first actuator is one of a lift actuator adapted to raise and lower the frame, a tilt actuator for changing a tilt of a pivotable section of the support surface, and a brake actuator for turning on and off a brake on the patient support apparatus.

15. The patient support apparatus of claim 13 wherein the patient support apparatus is one of a bed, stretcher, cot, recliner, or operating table.

16. The patient support apparatus of claim 13 wherein the computer forwards the first and second numbers to the second network service, and the second network service is adapted to gather the first and second numbers from a population of patient support apparatuses, analyze the first and second numbers, and use the analysis for determining the first and second thresholds.

17. A patient support apparatus comprising:

a frame;

a support surface supported on the frame;

a sensor;

a transceiver adapted to communicate with a remote network; and a controller supported on the patient support apparatus and in communication with the transceiver, the controller adapted to receive situational data from the sensor indicating a situational condition exists regarding a proximity of the patient support apparatus to at least one of a device, a person, and a location, to forward a message indicative of the existence of the situational condition to a network service hosted on the remote network, to receive from the network service a software application used to control a function related to the situational condition, and to execute the software application.

18. The patient support apparatus of claim 17 wherein the sensor detects the situational condition based upon the patient support apparatus being within a threshold proximity to the at least one of a device, a person, or a location.

19. The patient support apparatus of claim 17 wherein the situational condition is the presence of a mattress positioned on the patient support apparatus, the software application being adapted to be executed by the controller to enable the controller to control at least one aspect of the mattress.

20. The patient support apparatus of claim 17 wherein the situational condition is the presence of a patient entertainment device positioned within a common room with the patient support apparatus, the software application being adapted to be executed by the controller to enable a control positioned on the patient support apparatus to control an aspect of the patient entertainment device.

21. The patient support apparatus of claim 17 wherein the situational condition is the presence of a patient biological sensor, the software application being adapted to be used by the controller when communicating with the patient biological sensor.

22. The patient support apparatus of claim 17 wherein the situational condition is the presence of a second patient support apparatus, the software application being adapted to allow the controller to communicate with the second patient support apparatus.

* * * * *